(12) United States Patent
Shvilkin et al.

(10) Patent No.: US 11,701,049 B2
(45) Date of Patent: Jul. 18, 2023

(54) HAND HELD DEVICE FOR AUTOMATIC CARDIAC RISK AND DIAGNOSTIC ASSESSMENT

(71) Applicant: HEARTBEAM, INC., Santa Clara, CA (US)

(72) Inventors: Alexei Shvilkin, Chestnut Hill, MA (US); Ljupco Hadzievski, Belgrade (RS); Vladan Vukcevic, Belgrade (RS); Sanja Grujovic Zdolsek, Zemun (RS); Bosko Bojovic, Belgrade (RS)

(73) Assignee: HeartBeam, Inc., Santa Clara, CA (US)

( * ) Notice: Subject to any disclaimer, the term of this patent is extended or adjusted under 35 U.S.C. 154(b) by 0 days.

(21) Appl. No.: 17/296,669

(22) PCT Filed: Nov. 18, 2019

(86) PCT No.: PCT/US2019/061906
§ 371 (c)(1),
(2) Date: May 25, 2021

(87) PCT Pub. No.: WO2020/123102
PCT Pub. Date: Jun. 18, 2020

(65) Prior Publication Data
US 2022/0015679 A1    Jan. 20, 2022

Related U.S. Application Data

(60) Provisional application No. 62/780,782, filed on Dec. 17, 2018, provisional application No. 62/780,131, filed on Dec. 14, 2018.

(51) Int. Cl.
*A61B 5/332*     (2021.01)
*G16H 50/30*     (2018.01)
(Continued)

(52) U.S. Cl.
CPC .............. *A61B 5/332* (2021.01); *A61B 5/28* (2021.01); *A61B 5/7275* (2013.01); *G16H 50/30* (2018.01)

(58) Field of Classification Search
CPC ......... A61B 5/332; A61B 5/28; A61B 5/7275; G16H 50/20
(Continued)

(56) References Cited

U.S. PATENT DOCUMENTS

| 4,216,780 A | 8/1980 | Rubel |
| 4,850,370 A | 7/1989 | Dower |

(Continued)

FOREIGN PATENT DOCUMENTS

| CN | 1668242 A | 9/2005 |
| CN | 1870937 A | 11/2006 |

(Continued)

OTHER PUBLICATIONS

Dower et al.; A clinical comparison of three veg lead systems using resistance-combining networks; American Heart Journal; 55(4); pp. 523-534; Apr. 1958.
(Continued)

*Primary Examiner* — Carl H Layno
*Assistant Examiner* — Michael J Lau
(74) *Attorney, Agent, or Firm* — Shay Glenn LLP

(57) ABSTRACT

Method and apparatus for performing automatic cardiac diagnosis. The apparatuses described herein may be hand-held devices which enables self-recording of cardiac signals by the patient, including entering relevant data by patients regarding their cardiac history, including cardiac disease risk factors, and/or current conditions and symptoms. Based on recorded cardiac signals, cardiac risk factors and the current symptoms, the apparatus may calculates a cardiac risk score (Continued)

and may provide simplified diagnostic information and actionable instructions to the patient.

25 Claims, 10 Drawing Sheets

(51) Int. Cl.
*A61B 5/28* (2021.01)
*A61B 5/00* (2006.01)

(58) Field of Classification Search
USPC .......................................................... 600/509
See application file for complete search history.

(56) References Cited

U.S. PATENT DOCUMENTS

| | | | |
|---|---|---|---|
| 5,630,664 A | 5/1997 | Farrelly | |
| 5,724,580 A | 3/1998 | Levin et al. | |
| 6,047,203 A | 4/2000 | Sackner et al. | |
| 6,052,615 A | 4/2000 | Feild et al. | |
| 6,363,274 B1 | 3/2002 | Scalisi et al. | |
| 6,507,753 B1* | 1/2003 | Xue | A61B 5/349 128/923 |
| 6,607,480 B1 | 8/2003 | Bousseljot et al. | |
| 6,625,483 B2 | 9/2003 | Hoium et al. | |
| 6,636,274 B1 | 10/2003 | Mazda | |
| 7,266,408 B2 | 9/2007 | Bojovic et al. | |
| 7,477,935 B2 | 1/2009 | Palreddy et al. | |
| 7,647,093 B2 | 1/2010 | Bojovic et al. | |
| 7,801,591 B1* | 9/2010 | Shusterman | G16H 50/20 600/509 |
| 8,209,002 B2* | 6/2012 | Vajdic | A61B 5/349 600/512 |
| 8,369,936 B2 | 2/2013 | Farringdon et al. | |
| 8,615,290 B2 | 12/2013 | Lin et al. | |
| 8,676,304 B2* | 3/2014 | Fischell | A61B 5/352 607/9 |
| 8,700,137 B2 | 4/2014 | Albert | |
| 8,781,566 B2* | 7/2014 | John | A61B 5/349 600/509 |
| 8,818,482 B2 | 8/2014 | Phillips et al. | |
| 9,364,158 B2 | 6/2016 | Banet et al. | |
| 10,117,592 B2 | 11/2018 | Bojovic et al. | |
| 10,433,744 B2 | 10/2019 | Bojovic et al. | |
| 11,071,490 B1 | 7/2021 | Vajdic et al. | |
| 2002/0045836 A1 | 4/2002 | Alkawwas | |
| 2003/0032871 A1 | 2/2003 | Selker et al. | |
| 2003/0083586 A1 | 5/2003 | Ferek-Petric | |
| 2003/0083587 A1 | 5/2003 | Ferek-Petric | |
| 2004/0087864 A1 | 5/2004 | Grouse | |
| 2004/0138574 A1* | 7/2004 | Groenewegen | A61B 5/322 600/509 |
| 2005/0027203 A1 | 2/2005 | Umeda et al. | |
| 2005/0215918 A1 | 9/2005 | Frantz et al. | |
| 2005/0234354 A1 | 10/2005 | Rowlandson et al. | |
| 2006/0009698 A1 | 1/2006 | Banet et al. | |
| 2006/0224072 A1 | 10/2006 | Shennib | |
| 2007/0021677 A1 | 1/2007 | Markel | |
| 2008/0027330 A1 | 1/2008 | Naghavi et al. | |
| 2008/0113650 A1 | 5/2008 | Engstrom | |
| 2008/0161715 A1 | 7/2008 | Stivoric et al. | |
| 2009/0112105 A1 | 4/2009 | Clayman | |
| 2009/0281421 A1 | 11/2009 | Culp et al. | |
| 2009/0281440 A1 | 11/2009 | Farazi et al. | |
| 2009/0299206 A1 | 12/2009 | Wang et al. | |
| 2010/0023081 A1* | 1/2010 | Audet | A61B 5/02405 607/18 |
| 2010/0076331 A1 | 3/2010 | Chan et al. | |
| 2010/0130845 A1 | 5/2010 | Clayman | |
| 2010/0174204 A1 | 7/2010 | Danteny | |
| 2010/0240980 A1 | 9/2010 | Zhu et al. | |
| 2011/0015496 A1 | 1/2011 | Sherman et al. | |
| 2011/0105928 A1 | 5/2011 | Bojovic et al. | |
| 2011/0224565 A1* | 9/2011 | Ong | A61B 5/7275 600/509 |
| 2011/0301435 A1 | 12/2011 | Albert et al. | |
| 2011/0306859 A1 | 12/2011 | Saldivar et al. | |
| 2012/0022385 A1 | 1/2012 | Shimuta et al. | |
| 2012/0059271 A1 | 3/2012 | Amitai et al. | |
| 2012/0116176 A1 | 5/2012 | Moravec et al. | |
| 2012/0116240 A1 | 5/2012 | Chou | |
| 2012/0136266 A1* | 5/2012 | Grady | G16H 40/63 600/509 |
| 2012/0184858 A1 | 7/2012 | Harlev et al. | |
| 2012/0283586 A1 | 11/2012 | Song et al. | |
| 2013/0125906 A1 | 5/2013 | Hon | |
| 2013/0172723 A1 | 7/2013 | Baxi et al. | |
| 2014/0114166 A1 | 4/2014 | Baxi | |
| 2014/0155723 A1 | 6/2014 | Levin et al. | |
| 2014/0163349 A1 | 6/2014 | Amitai et al. | |
| 2014/0257122 A1* | 9/2014 | Ong | A61B 5/316 705/2 |
| 2015/0018660 A1 | 1/2015 | Thomson et al. | |
| 2015/0057512 A1 | 2/2015 | Kapoor | |
| 2016/0015286 A1 | 1/2016 | Gitlin et al. | |
| 2016/0022162 A1 | 1/2016 | Ong et al. | |
| 2016/0045166 A1* | 2/2016 | Gheeraert | A61B 5/35 600/509 |
| 2016/0135706 A1 | 5/2016 | Sullivan et al. | |
| 2016/0188823 A1 | 6/2016 | Rowlandson et al. | |
| 2016/0287172 A1 | 10/2016 | Morris et al. | |
| 2017/0127966 A1 | 5/2017 | Wu et al. | |
| 2017/0188861 A1 | 7/2017 | Schreck et al. | |
| 2017/0290522 A1* | 10/2017 | Bojovic | G16H 40/63 |
| 2018/0004904 A1* | 1/2018 | Phillips | G16H 50/30 |
| 2018/0064356 A1 | 3/2018 | Mendenhall et al. | |
| 2019/0069789 A1 | 3/2019 | Bojovic et al. | |
| 2019/0117100 A1 | 4/2019 | Rollie et al. | |
| 2019/0336020 A1 | 11/2019 | Kranz | |
| 2020/0113454 A1 | 4/2020 | Wu et al. | |
| 2020/0315480 A1 | 10/2020 | Hwang | |
| 2020/0375493 A1 | 12/2020 | Kranz | |
| 2021/0113136 A1 | 4/2021 | Bojovic et al. | |
| 2022/0015680 A1 | 1/2022 | Vajdic et al. | |
| 2022/0125363 A1 | 4/2022 | Vajdic et al. | |

FOREIGN PATENT DOCUMENTS

| | | |
|---|---|---|
| CN | 101524272 A | 9/2009 |
| CN | 202854760 U | 4/2013 |
| CN | 203000927 U | 6/2013 |
| EP | 1227752 A1 | 8/2002 |
| EP | 0944353 B1 | 11/2002 |
| EP | 1659936 A1 | 3/2005 |
| WO | WO01/70105 A2 | 9/2001 |
| WO | WO2017/208040 A2 | 12/2017 |
| WO | WO2020/0232040 A1 | 11/2020 |

OTHER PUBLICATIONS

Goff et al.; 2013 ACC/AHA guideline on the assessment of cardiovascular risk: a report of the American College of Cardiology/American Heart Association Task Force on Practice Guidelines; Journal of the American College of Cardiology; 63(25 Part B); pp. 2935-2959; Jul. 1, 2014.

Kligfield et al.; Recommendations for the standardization and interpretation of the electrocardiogram: Part I: The Electrocardiogram and its Technology A Scientific Statement From the American Heart Association Electrocardiography and Arrinythmias Committee, Council on Clinical Cardiology; the American College of Cardiology Foundation; and the Heart Rhythm Society Endorsed by the International Society for Computerized Electrocardiology; 49(10); pp. 1109-1127; Mar. 13, 2007.

Marma et al.; Systematic examination of the updated Framingham heart study general cardiovascular risk profile; Circulation; 120(5): pp. 384; Aug. 1, 2009.

Med-Tech Innovation; The ECG device the of a credit card; Aug. 23, 2017; retrieved from the internet (https://www.med-technews.com/news/the-ecg-device-the-size-of-a-credit-card/) on Jan. 26, 2021.

(56) References Cited

OTHER PUBLICATIONS

Perk et al.: European Guidelines on cardiovascular disease prevention in clinical practice (version 2012) The Fifth Joint Task Force of the European Society of Cardiology and Other Societies on Cardiovascular Disease Prevention In Clinical Practice; European heart Journal; 33(13); pp. 1635-1701; Jul. 1, 2012.
Goff et al.; 2013 ACC/AHA guideline on the assessment of cardiovascular risk: a report of the American College of Cardiology/American Heart Association Task Force on Practice Guidelines; Journal of the American College of Cardiology;; 129(25 Suppl 2); pp. S49-S73; Jun. 2014.
Rakshit et al.; EKF with PSO technique for delineation of P and T wave in electrocardiogram (ECG) signal; in 2015 2nd International Conference on Signal Processing and Integrated Networks (SPIN); IEEE; pp. 696-701; Feb. 19, 2015.
Sun et al.; Characteristic wave detection in ECG signal using morphological transform; BMC cardiovascular disorders; 5(1); pp. 1-7; Dec. 2005.
Belicev et al.; U.S. Appl. No. 17/494,806 entitled "Method and apparatus for reconstructing electrocardiogram (ECG) data," filed Oct. 5, 2021.
Vajdic et al.; U.S. Appl. No. 17/609,014 entitled "Compact mobile three-lead cardiac monitoring device," filed Nov. 5, 2021.
Vajdic ; U.S. Appl. No. 17/726,497 entitled "Apparatus for generating an electrocardiogram," filed Apr. 21, 2022.
Belicev et al.; U.S. Appl. No. 17/948,099 entitled "Method and apparatus for reconstructing electrocardiogram (ECG) data," filed Sep. 19, 2022.
Vajdic; U.S. Appl. No. 18/068,481 entitled "Apparatus for generating an electrocardiogram," filed Dec. 19, 2022.

\* cited by examiner

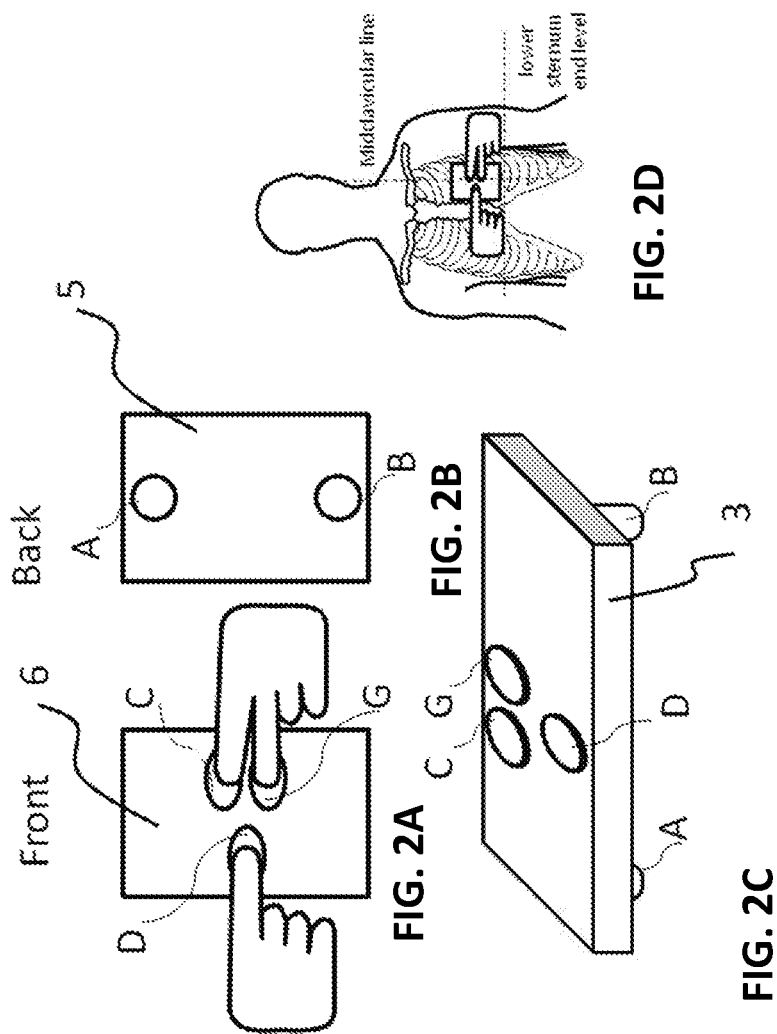

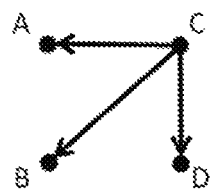
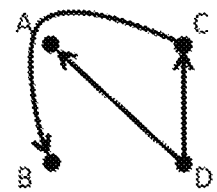
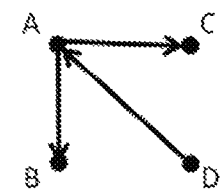
FIG. 4E          FIG. 4F          FIG. 4G
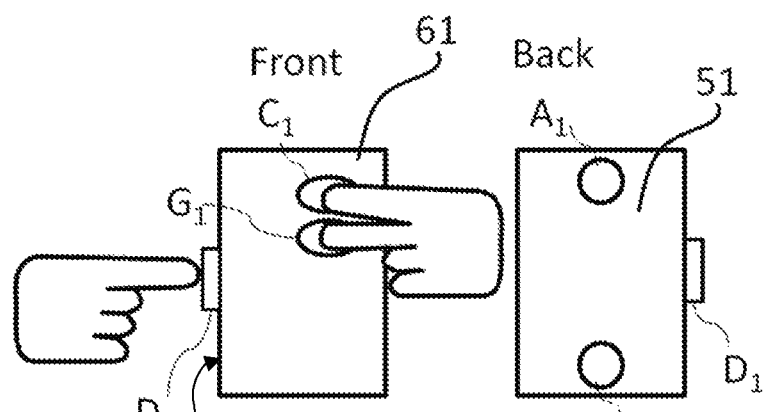
FIG. 5A          FIG. 5B
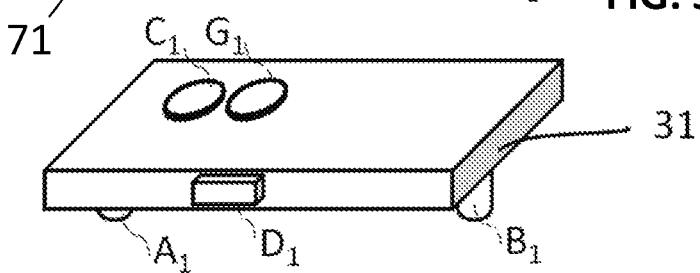
FIG. 5C

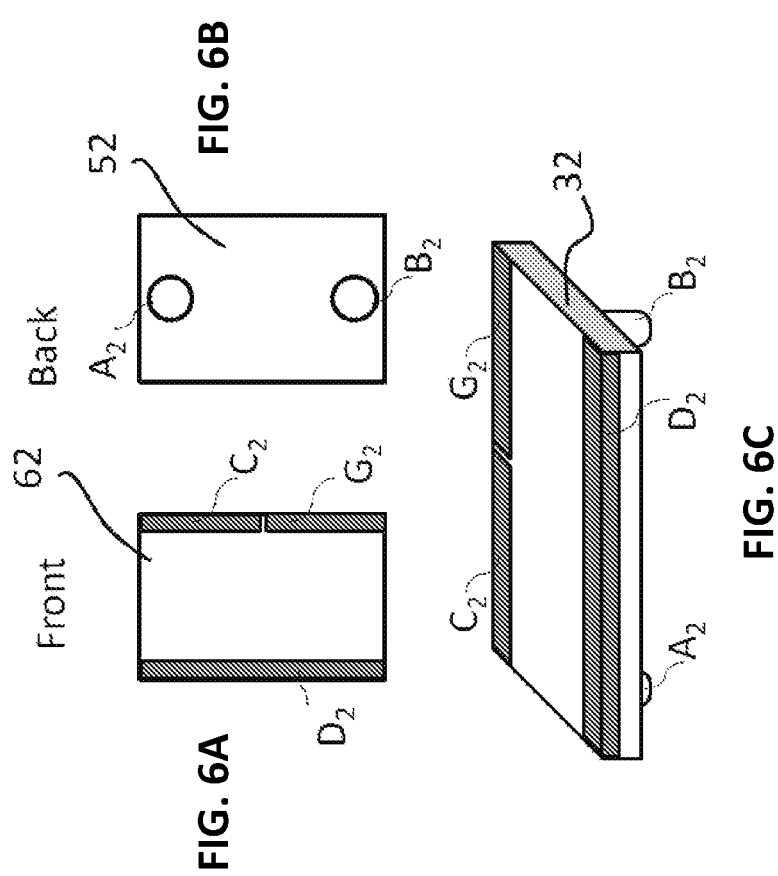

| | | | |
|---|---|---|---|
| 1.1 | Location: Exclusive* | Substernal | 3 |
| 1.2 | | Precordial | 2 |
| 1.3 | | Neck, Jaw, Epigastrium | 1 |
| 1.4 | | Left chest | -1 |
| 1.5 | | Right chest | 1 |
| 1.6 | | Back | 0 |
| 1.7 | | Other | 0 |
| 2.1 | Pain area size: Exclusive | Less than a coin | -1 |
| 2.2 | | More than a coin | 1 |
| 3.1 | Radiation: Exclusive | Left or right arm | 2 |
| 3.2 | | Both shoulders or right shoulder | 3 |
| 3.3 | | Left Shoulder, or back, or neck, or lower jaw | 1 |
| 3.4 | | Abdomen, or lower back | -1 |
| 3.5 | | Other | 0 |
| 3.6 | | None | 0 |
| 4.1 | Characteristics: Exclusive | Crushing, pressing, squeezing | 3 |
| 4.2 | | Heaviness, tightness | 2 |
| 4.3 | | Burning/aching | 1 |
| 4.4*** | Only for pts with CHD, angina | Similar or worse than previous angina | 3 |
| 4.5 | | Sticking, stabbing, catching, pinprick | -1 |
| 4.6 | | Other | 0 |
| 5.1 | Aggravated by : Exclusive | Gets worse with exertion, makes you stop/slow down | 2 |
| 5.2 | | Gets worse with deep breath, cough | -1 |
| 5.3 | | Constant, not changing | 0 |
| 6.1 | Associated symptoms: Additive** | Nausea or vomiting | 2 |
| 6.2 | | Dyspnea | 2 |
| 6.3 | | Diaphoresis | 3 |
| 6.4 | | None | 0 |
| 7.1 | Duration : Exclusive | Intermittent (momentary) or < 2 min at a time | -1 |
| 7.2 | | 2-15 min | 1 |
| 7.3 | | 15-60 min | 1 |
| 7.4 | | 60 min – 12 hrs | 0 |
| 7.5 | | > 12 hrs | -1 |
| 8..1 | Frequency : Exclusive | >=2 per 24 hrs | 1 |
| 8.2 | | 1 or less per 24 hrs | 0 |
| 9.1 | Additional characteristics: Exclusive | Reproduces or worsens by palpation | 1 |
| 9.2 | | Not sensitive on palpation | 0 |

*exclusive – only single answer
**additive – multiple answers
*** 4.4 might be chosen with one of the other options of group 4.

FIG. 9

| Risk factors | Risk level | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Combinations | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
| 1. Pre existing (PER) | H | H | H | H | H | H | H | H | H | I | I | I | I | I | I | I | I | I | L | L | L | L | L | L | L | L | L |
| 2. Chest pain (CPR) | H | H | H | I | I | I | L | L | L | H | H | H | I | I | I | L | L | L | H | H | H | I | I | I | L | L | L |
| 3. Cardiac signals (CSR) | H | I | L | H | I | L | H | I | L | H | I | L | H | I | L | H | I | L | H | I | L | H | I | L | H | I | L |
| Post test AMI risk (PTR) | H | H | H | H | H | H | H | I | L | H | H | H | H | I | L | H | L | L | H | H | I | H | I | L | H | L | L |

FIG. 10

HAND HELD DEVICE FOR AUTOMATIC CARDIAC RISK AND DIAGNOSTIC ASSESSMENT

CROSS REFERENCE TO RELATED APPLICATIONS

This application claims priority to U.S. Provisional Patent Application No. 62/780,131 filed Dec. 14, 2018 titled "HAND HELD DEVICE FOR AUTOMATIC CARDIAC RISK AND DIAGNOSTIC ASSESSMENT" and U.S. Provisional Patent Application No. 62/780,782 filed Dec. 17, 2018 titled "HAND HELD DEVICE FOR AUTOMATIC CARDIAC RISK AND DIAGNOSTIC ASSESSMENT".

This patent application may be related to U.S. patent application Ser. No. 15/096,159, filed on Apr. 4, 2016 titled "MOBILE THREE-LEAD CARDIAC MONITORING DEVICE AND METHOD FOR AUTOMATED DIAGNOSTICS", which claimed priority to U.S. Provisional Patent Application No. 62/145,431 titled "MOBILE THREE-LEAD CARDIAC MONITORING DEVICE AND METHOD FOR AUTOMATED DIAGNOSTICS" filed Apr. 9, 2015; each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are methods and devices for diagnosis of cardiac conditions. In particular, described herein are hand-held devices for self-diagnosis of cardiac conditions. For example, described herein are three-lead cardiac signal acquisition and processing devices configured to assess a patient's risk of a serious condition such as AMI (Acute Myocardial Infarction, or heart attack) or cardiac ischemia (the underlying physiological process in AMI).

BACKGROUND

A number of solutions have been developed for risk assessment of serious cardiac conditions. In many cases, these methods may include recorded cardiac signals as input data, as well as other medical data typically entered through a user interface. These solutions are typically aimed at providing support to professional medical staff in setting proper diagnosis. Examples of such devices may be found in Selker et. al (US20030032871), Farrelly (U.S. Pat. No. 5,630,664), Grouse (US20040087864), Rowlandson et al. (US20160188823), Rowlandson et al. (US20050234354), Levin et al. (U.S. Pat. No. 5,724,580), and Sackner (U.S. Pat. No. 6,047,203). These methods and apparatuses may provide some information on cardiac condition risk, however, such devices are either relatively complicated to handle, involving the use of several components, or are not capable of assessing most serious heart conditions. All the solutions mentioned above are primarily intended as an aid to a general practitioner physician or a cardiologist when assessing risk of cardiac death or setting a cardiac diagnosis, and require professional medical interpretation of the obtained results.

Thus, there remains a need for self-contained devices which are simple to use, capable of being operated by a patient experiencing symptoms that may relate to an ongoing AMI, and that can provide a user interface that gives the patient a diagnostic advice on steps that the patient should take based on their immediate needs. Further, there is a need for apparatuses and methods that enable a cardiac patient suffering symptoms suggestive of AMI to record his cardiac signals without using cables and provide automatic clinical advice. Described herein are methods and apparatuses (including systems and/or devices) that may address these needs.

SUMMARY OF THE DISCLOSURE

Described herein are self-contained devices which may be configured to be simple to use, capable of being operated by a patient experiencing symptoms related to an ongoing cardiac event (such as, but not limited to AMI), that can store data on patient's cardiac risk factors, record the patient's cardiac signals, which include a user interface that enables the patient to enter data on the current symptoms, and that provide a user interface that gives the patient a diagnostic advice on steps that the patient should take. These devices may record and analyze a patient's ECG without using cables, and can manipulate data about the patient's risk factors and current symptoms to provide automatic clinical advice.

For example, described herein are methods and apparatuses (e.g., devices and/or systems) that may enable automatic diagnosis of heart conditions. Such an apparatus may determine a patient's risk score and provide real-time advice to the patient based on the risk score, where the risk-score is based on at least three components: cardiac signal risk (CSR), pre-existing risk (PER) for the patient (which may be stored in a memory), and a chest pain risk (CPR—current symptoms risk). The apparatus may perform an evaluation of cardiac conditions which includes several phases.

For example, the apparatus may first acquire three types of data, related to the three risk components, namely: the cardiac data, preexisting risk data and current symptoms risk data. The cardiac data may be acquired by means of a hand-held cardiac device, enabling self-recording of the cardiac signals by the patient—without medical staff assistance and capturing three-dimensional cardiac signal information, and particularly those cardiac devices that acquire three orthogonal leads (such as those disclosed in patent document US20170290522, herein incorporated by reference in its entirety). The device may include at least two integral chest electrodes and at least two integral hand electrodes, with no cables, and may be capable of recording three substantially orthogonal leads from these four (or more) electrodes. The three orthogonal leads may be formed by using different electrode configurations with or without a resistive network having a central point. Alternatively or additionally, other devices may be used, such as, e.g., U.S. Pat. No. 7,647,093 (which uses 12-leads ECG synthesized based on three orthogonal leads), herein incorporated by reference in its entirety. Also, other hand-held ECG devices that can measure [www.shl-telemedicine.com/], www.aerotel.com/) or synthesize (U.S. Pat. No. 4,850,370A) 12-leads ECG may alternatively be used.

The apparatus may perform a baseline recording of the first set of three orthogonal leads that may be stored in a memory (e.g., register). During diagnostic recording, a second set of three orthogonal leads may be taken, and a difference signal between the two sets may be determined.

The recorded cardiac signals represented by the parameters of cardiac signals baseline recording, diagnostic recording and difference signal may be transmitted to an internal processor and/or may be wirelessly transmitted to a remote processor for processing as will be described in greater detail herein. The apparatus may be a standalone device, as an integral part of a modified mobile phone, and/or as an extension structure thereof. In the latter case, it may be a mobile phone back cover or mobile phone protective case.

The two other risk components may be entered manually by means of a keyboard or touch screen, or may be received (e.g., via wireless transmission) or recalled from a remote or local memory. For example, the second type data, related to the preexisting risk, may be entered and stored in the apparatus internal memory for further processing, which may occur before the apparatus is put in use. Current symptoms risk data may be entered at the time the cardiac symptoms occur, i.e. as the cardiac signals recording takes place. For the purpose of entering other types of data, the hand-held apparatus may be additionally equipped with a graphical user interface capable of entering preexisting risk data, which may be entered by medical staff, as well as the current symptoms risk data which may be entered by the patient.

Following data acquisition, the apparatus may process the data on the basis of three types of input data.

Each risk may be described with three risk levels, for example: H—High, I—Intermediate, L—Low. The values of three risk components, CSR, PER and CPR, may be used in a scoring model to evaluate the post-test risk (PTR) with three risk levels: H—High, I—Intermediate, L—Low. The post-test risk value may be used to choose the diagnostic message communicated to the patient.

The last phase is related to providing the patient with the diagnostic information, e.g., by sending a textual message via a graphical user interface. The message may instruct the user to call an emergency service, wait for another measurement or reassure the user regarding the benign nature of the symptoms. In other words, the message may have a form of instructions for the patient about what action actions to take.

In some embodiments, parameters of the three risk components CSR, PER and CPR, may be used to choose the diagnostic message in addition to the values of three risk components. For example, parameters such as the existence of the angina pectoris (a component of PER), or high ST elevation (a component of CSR), persistent chest pain (a component of CPR) may be used. Based on the presence or absence of one or more of these parameters, the apparatus may modify the scoring (e.g., the apparatus may include a separate decision paths for patients with and without angina pectoris, an element of the pre-existing risk (PER) data).

The apparatus may also be configured to consider dynamic diagnostic signs, such as cardiac signals parameters and symptoms, for heart attack diagnostics. For example, chest pain consistent with heart attack is often persistent or increasing, while anginal pain is triggered by physical activity, and is relieved after the activity stops. Therefore, in some embodiments the apparatus may require the patient to repeat the diagnostic session: the cardiac signals recording and filling the questionnaire about current symptoms (chest pain questionnaire—CPQ), more than once in predefined intervals before the final diagnostic message is given to the patient. In this case the final diagnostic assessment may be created using values of the PER and the values of the CSR, CPR and PTR risks in the diagnostic sessions performed by the patient in predefined time intervals, such as three sessions with 5-10 minutes time intervals. Also, repeating the cardiac signals recording by the patient may reduce the probability of basing the diagnostic decision on a single recording with bad signal quality. The apparatuses and methods described herein may allow a patient to self-record and automatically diagnose serious cardiac conditions, and may provide improved accuracy in calculating cardiac risk. Thus, these apparatuses may be capable of recording baseline cardiac signal and cardiac risk factors of the patient, storing them in the device memory prior to the diagnostic use of the device, and recording diagnostic ECG and symptoms data at the time the cardiac symptoms occur. Manually entered patient related data (e.g., risk factors and current symptoms) may be crucial for automatic urgent cardiac diagnosis, because, the cardiac signal recording taken in isolation from other clinical data has limited diagnostic value and can suffer from low accuracy and precision due to measurement interference.

For example, described herein are methods of automatically assessing a patient's risk of an acute cardiac risk. These methods may include: receiving, from the patient, risk assessment information comprising risk factors, wherein the risk assessment information is received by a processor; storing a pre-existing risk score based on the risk assessment information; receiving, from the patient, a sample cardiac signals, wherein the patient self-records the sample cardiac signals using a wireless hand-held apparatus, and receiving, from the patient, a current symptoms indication; determining, in the processor, an cardiac signals risk score from the sample cardiac signals and a baseline cardiac signals, and a chest pain risk score based on the current symptoms indication, and using the cardiac signals risk score, the pre-existing risk score, and the chest pain risk score to determine a post-test risk score; and presenting, to the patient, a diagnostic report and patient action instruction based on the post-test risk score.

For example, a method of automatically assessing a patient's risk of an acute cardiac risk may include: receiving, from the patient at a first time, a baseline cardiac signals, wherein the patient uses a wireless hand-held apparatus having at least four electrodes to acquire three substantially orthogonal leads, wherein the baseline cardiac signals is received by a processor; storing the baseline cardiac signals in a first memory accessible to the processor; receiving, from the patient at a second time, risk assessment information, wherein the risk assessment information is received by the processor; storing a pre-existing risk score based on the risk assessment information in a second memory accessible by the processor; receiving, from the patient at a third time that is more than a day from the first time, a sample cardiac signals, wherein the patient self-records the sample cardiac signals using the wireless hand-held apparatus and a current symptoms indication, wherein the current symptoms indication is selected from a predetermined list of symptom selectable on the wireless hand-held apparatus; determining, in the processor, an cardiac signals risk score from the sample cardiac signals and the baseline cardiac signals, and a chest pain risk score based on the current symptoms indication, and using the cardiac signals risk score, the pre-existing risk score, and the chest pain risk score to determine a post-test risk score; and presenting, to the patient, a diagnostic report and patient action instruction based on the post-test risk score.

For example, a method of automatically assessing a patient's risk of an acute cardiac risk may include: receiving, from the patient at a first time, a baseline cardiac signals, wherein the patient uses a wireless hand-held apparatus having at least four electrodes to acquire three substantially orthogonal leads, wherein the baseline cardiac signals is received by a processor; storing the baseline cardiac signals in a first memory accessible to the processor; receiving, from the patient at a second time, risk assessment information comprising risk factors including: age, total cholesterol, HDL, systolic blood pressure, diabetes mellitus status, and current smoking status, wherein the risk assessment information is received by the processor; storing a pre-existing risk score based on the risk assessment information in a second memory accessible by the processor; repeating, when the patient is experiencing cardiac distress at a third time that is more than a day from the first time, the steps of: receiving, from the patient, a sample cardiac signals, wherein the patient self-records the sample cardiac signals using the wireless hand-held apparatus and a current symptoms indication, wherein the current symptoms indication is selected from a predetermined list of symptom selectable on the wireless hand-held apparatus; determining, in the processor, an cardiac signals risk score from the sample cardiac signals and the baseline cardiac signals, and a chest pain risk score based on the current symptoms indication, and using the cardiac signals risk score, the pre-existing risk score, and the chest pain risk score to determine a post-test risk score; and presenting, to the patient, a diagnostic report and patient action instruction based on the post-test risk score.

Also described herein are apparatuses configured to perform any of these methods, including, for example, a non-transitory computer-readable storage medium storing a set of instructions capable of being executed by a processor, that when executed by the processor causes the processor to automatically assesses a patient's risk of an acute cardiac risk by: receiving, from the patient, risk assessment information comprising risk factors, wherein the risk assessment information is received by a processor; storing a pre-existing risk score based on the risk assessment information; receiving, from the patient, a sample cardiac signals, wherein the patient self-records the sample cardiac signals using a wireless hand-held apparatus, and receiving, from the patient, a current symptoms indication; determining, in the processor, an cardiac signals risk score from the sample cardiac signals and a baseline cardiac signals, and a chest pain risk score based on the current symptoms indication, and using the cardiac signals risk score, the pre-existing risk score, and the chest pain risk score to determine a post-test risk score; and presenting, to the patient, a diagnostic report and patient action instruction based on the post-test risk score.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2A shows a front (non-chest) view of one variation of a handheld device with two recording and one ground electrode.

FIG. 2B shows a back (chest) view of one variation of a handheld device with two recording electrodes.

FIG. 2C shows an axonometric view of a handheld device.

FIG. 2D shows a front view of the device placed against the patient's body in a recording position.

FIGS. 4E, 4F and 4G show schematic diagrams of three possible configurations for measuring 3 leads among two chest and two hand electrodes.

FIG. 5A shows a front (non-chest) view of the handheld device with two front and one side electrode.

FIG. 5B shows a back (chest) view of the handheld device with two front and one side electrode.

FIG. 5C shows an axonometric view of the handheld device with two front and one side electrode.

FIG. 6A is a front (non-chest) view of the handheld device with electrodes on the edges of the device.

FIG. 6B is a back (chest) view of the handheld device with electrodes on the edges of the device.

FIG. 6C is an axonometric view of the handheld device with electrodes on the edges of the device.

FIG. 9 is a table illustrating a list of parameters-questions that may be used to estimate chest pain risk (CPR) as described herein.

FIG. 10 is a table illustrating one example of a method of assessing AMI risk as described herein.

DETAILED DESCRIPTION

Figure 1A:
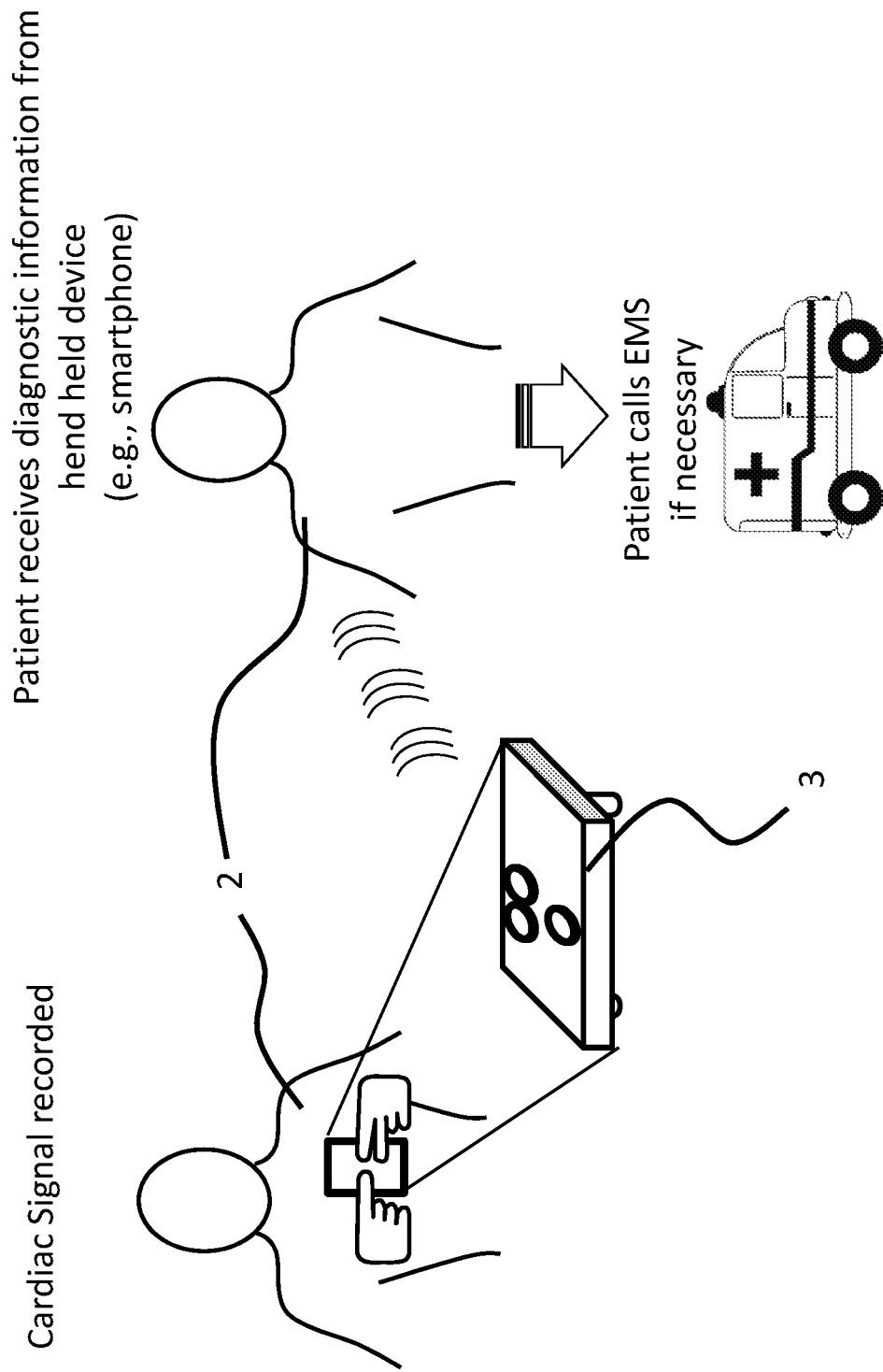
FIG. 1A shows one variation of a schematic configuration of a diagnostic system for detection of cardiac disorders such as AMI, including a local processor in the system.

The methods and apparatuses for automatic remote diagnosis of heart conditions described herein may include automated diagnostic methods and the improved handheld cardiac apparatuses. These methods and apparatuses may implement a risk scoring model based on three risk components: pre-existing risk related to the patient's risk factors, chest pain risk related to current symptoms risk, and the recorded cardiac signals. Since these methods and apparatuses use risk factors and current symptoms as additional input, in addition to recording three orthogonal cardiac signals leads, not only AMI, but other cardiac conditions such as angina pectoris can be detected. In addition, using manually entered patient related data may provide for accurate setting of cardiac diagnosis, particularly in instances where an cardiac signals recording has low accuracy and precision, e.g., due to measurement interference. Thus, the methods and apparatuses described herein may improve the operation of current solutions by enabling not only automatic diagnostics of serious cardiac conditions but high accuracy diagnosis. The methods and apparatuses may be configured to include data acquisition, data processing (e.g., applying a scoring model) and sending diagnostic information to the patient about his heart conditions. The method may be performed on an apparatus configured as a handheld device that enables entering patient related data (e.g., preexisting risk and current symptoms risk data), recording of cardiac signals by the patient and retrieving previously stored cardiac risk related data, in the situation where symptoms relate to an ongoing AMI or in similar situation. The device may include a user interface for entering patient's cardiac risk factors data and current symptoms data in textual form, as well as a memory for storing patient's cardiac risk factors data. Upon acquisition, the data may be transmitted to a remote processor. The processor may be configured to provide the patient with diagnostic information and transmit the diagnostic information back to the handheld device. The patient may decide, based on the received information, to take further actions, such as calling for emergency medical care. The handheld device may communicate the diagnostic information to the patient via characteristic sounds, voice messages or via a graphical display. The processor may be configured via hardware, software, firmware, or the like, and may process the signals may be received to produce a difference signal and extract information reliably related to detection of AMI.

For example, a handheld device may be configured to be operated by a patient when cardiac symptoms occur. The device may include a storage (e.g., memory) for storing data on patient's cardiac risk factors and other data, cardiac signals recording components (e.g., electrodes, circuitry, controller) for recording a patient's cardiac signals; the recording components may be similar to those disclosed in [WO2016/164888A1, Bojovic et al], mentioned above. Patient related data (risk factors and current symptoms) may be entered and diagnostic message may be communicated to the patient, by equipping the device with a graphical user interface (e.g., touch screen or screen and a keyboard, etc.). The diagnostic information can also or alternatively be communicated to the patient via speaker through characteristic sounds or voice messages.

The apparatus may be configured to record three, substantially orthogonal, cardiac signals leads, and may therefore include at least two chest electrodes, and at least two non-chest electrodes for contacting parts of each of the patient's hands, preferably for contacting fingers. The non-chest electrodes may be integrated at the front and/or at the sides of the device. In some electrode configurations, the device may have a ground electrode integrated anywhere at the surface of the device.

Specifically, described herein are 3-lead cardiac recording devices for user placement on the chest, which include an arrangement of electrodes on both the front and back (and in some variations, one or more sides) so that the devices may be held by both of the user's hand in a predefined orientation, so as to record a 3 orthogonal lead cardiac signals when held against the user's chest. In order to fulfill above described functions, the handheld device may record three leads without using cables (e.g., may include only surface electrodes held or held against the body). Further, the resulting three leads are non-coplanar, and as close to orthogonal as possible.

The handheld devices described herein may include at least four recording electrodes. An optional fifth electrode may be used, e.g., four recording electrodes and one ground electrode. Typically, the handheld device may include two chest electrodes which are the recording electrodes, and may be located on the back side of the device. The remaining non-chest electrodes may be used for collecting cardiac signals from the fingers of the right and left hand and the optional third one may be used as the ground electrode.

The handheld devices may have various electrode configurations for recording three orthogonal cardiac lead signals. In one embodiment, the handheld device has two chest recording electrodes, one recording finger electrode on the left side of the device and two finger electrodes on the front side of the device, one recording and one ground electrode. The optimal position of the handheld device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum.

In another embodiment, the ground electrode may be excluded from the configuration, which may give acceptable 50-60 Hz electrical noise performance if a ground-free signal amplifier configuration is used. A four recording electrode configuration (e.g., having two chest and two finger electrodes) may also fulfill the condition of high orthogonality discussed above. The simplest way to fulfill this requirement may be to record signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, we use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kOHM each, or unequal, the first one approximately 5 kOHM between the left-hand electrode and the CP, and the second one approximately 10 kOHM between the right hand electrode and the CP. This asymmetry reflects the left-side position of the heart in the torso, thus shifting the CP at the approximate electrical center of the heart. In this way, we obtain a three lead system that are substantially orthogonal.

Other similar lead configurations with the same CP may be chosen using the same set of two chest and two hand electrodes. Such a lead configuration may be substantially orthogonal, for example when both chest electrodes are used to record leads with the reference pole at the CP. Another possibility to define CP is using three electrodes, two hand electrodes and one chest electrode, and 3 resistors connected in a Y (star) configuration.

Other lead configurations without CP may also be used, like the configuration recording the signal of two chest electrodes and right-hand electrode with respect to left hand electrode. Such configurations without resistors or CP are more noise resistant to, for example, 50-60 Hz electrical noise, but have less orthogonal lead directions than the described ones using a CP. Generally, any other lead configuration using the same four described electrodes (a total of 20 configurations without a CP) results in leads that are non-coplanar and as such capture diagnostic signal in all three directions, but may lack a high degree of orthogonality. However, these configurations may have different levels of orthogonality, depending on the use of the right-hand electrode. The configuration using the right-hand electrode as the common reference pole in all 3 leads may have the lowest orthogonality, since the right-hand electrode is farthest from the heart among the four electrodes, and thus the angles between the vectors corresponding to the three leads are the smallest. However, this configuration with the lowest orthogonality is optimal for reconstruction of 12 leads ECG based on 3 lead signal, due to its small non-dipolar content, as described in patent document [U.S. Pat. No. 7,647,093, Bojovic et al]. Nevertheless, the signals obtained using this configuration may be used with or without 12 leads reconstruction The effectiveness of the described solution is not affected if one or more chest electrodes are added on the back side of the device, and one or more corresponding additional leads are recorded and used in diagnostic algorithms. Also, the effectiveness will not be affected if front electrodes are pressed with palms or any other part of hands instead with the fingers.

For example, the apparatuses described herein may be used for remote diagnostics of cardiac conditions, such as acute myocardial infarction (AMI), atrial fibrillation (AFib), or the like. In particular, described herein are handheld devices with special electrode configurations capable of recording three orthogonal cardiac lead signals in an orientation-specific manner, and transmitting these signals to a processor (e.g., PC or other computing device). The processor may be configured to diagnose/detect AMI and transmit the diagnostic information back to the handheld device. The handheld device may communicate the diagnostic information to the patient via characteristic sounds, voice messages or via a graphical display. The processor may be configured via hardware, software, firmware, or the like, and may process the signals received to produce a difference signal and extract information reliably related to detection of AMI (and additional information of clinical relevance). Thus, these apparatuses and methods may perform automated detection of cardiac conditions on the basis of a 3-lead system, without the necessity for 12 L ECG reconstruction, reducing or eliminating the need for medical personnel to interpret the ECG, unlike prior art systems, which typically rely on medical personnel for such decisions. The automated diagnostic methods described herein, in combination with the improved handheld cardiac devices, address many of the needs and problems present in other systems.

Specifically, described herein are 3-lead cardiac recording devices for user placement on the check, which include an arrangement of electrodes on both the front and back (and in some variations, one or more sides) so that the devices may be held by both of the user's hand in a predefined orientation, so as to record a 3 lead cardiac signals when held against the user's chest. In order to fulfill above described functions, the handheld device may record three leads without using cables (e.g., may include only surface electrodes held or held against the body). Further, the resulting three leads are non-coplanar, and as close to orthogonal as possible. Finally, at least one electrode may be mounted on the front side of the device (opposite to the chest side), to produce the force needed to hold device against the chest.

Unlike prior art devices, there is no requirement for low, non-dipolar content, as the apparatuses and methods described herein do not require reconstruction of 12 L ECG from the measured 3 leads.

The handheld devices described herein are configured to be mechanically stable and allow good electrical contact with the chest and to eliminate possibility for switching of finger contacts. The handheld devices described herein may include five electrodes, e.g., four recording electrodes and one ground electrode. Typically, the handheld device may include two chest electrodes which are the recording electrodes, and may be located on the back side of the device. The remaining three non-chest electrodes may be used for collecting cardiac signals from the fingers of the right and left hand and the third one may be used as the ground electrode. At least one of these three non-chest electrodes may be mounted on the front side for pressing with the fingers in order to produce enough pressure to hold the device against the chest. Finally, the requirement of avoiding finger switching may be fulfilled by an asymmetric electrode configuration. For example, one of the three non-chest electrodes may establish contact with one finger of the first hand, and the remaining two electrodes may establish contact with the other hand. One of these two electrodes may be used as common ground electrode and the other may be used for signal measuring. An example of such configuration has two chest recording electrodes, one recording finger electrode on the left side of the device and two finger electrodes on the front side of the device, one recording and one ground electrode. The optimal position of the handheld device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum.

In another embodiment, the ground electrode may be excluded from the configuration, which may give acceptable 50-60 Hz electrical noise performance if a ground-free signal amplifier configuration is used. A four recording electrode configuration (having two chest and two finger electrodes) may also fulfill the condition of high orthogonality discussed above. The simplest way to fulfill this requirement is to record signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, we use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kΩ each, or unequal, the first one approximately 5 kΩ between the left hand electrode and the CP, and the second one approximately 10 kΩ between the right hand electrode and the CP. This asymmetry reflects the left-side position of the heart in the torso, thus shifting the CP at the approximate electrical center of the heart. In this way we obtain a three lead system that are substantially orthogonal.

Other similar lead configurations with the same CP may be chosen using the same set of two chest and two hand electrodes, with the distance between the chest electrodes in caudal direction at least 5 cm, preferably greater than about 10 cm. Such a lead configuration may be substantially orthogonal, for example when both chest electrodes are used to record leads with the reference pole at the CP. Another possibility to define CP is using three electrodes, two hand electrodes and one chest electrode, and 3 resistors connected in a Y (star) configuration.

Other lead configurations without CP may also be used, like the configuration recording the signal of two chest electrodes and right hand electrode with respect to left hand electrode. Such configurations without resistors or CP are more noise resistant to, for example, 50-60 Hz electrical noise, but have less orthogonal lead directions than the described ones using a CP. Generally, any other lead configuration using the same four described electrodes (a total of 20 configurations without a CP) results in leads that are non-coplanar and as such capture diagnostic signal in all three directions, but may lack a high degree of orthogonality. However, these configurations may have different levels of orthogonality, depending on the use of the right hand electrode. The configuration using the right hand electrode as the common reference pole in all 3 leads may have the lowest orthogonality, since the right hand electrode is farthest from the heart among the four electrodes, and thus the angles between the vectors corresponding to the three leads are the smallest. The configurations using right hand electrode in two leads have better orthogonality, while best orthogonality is achieved in the configurations using right hand electrode in only one lead.

The effectiveness of the described solution is not affected if one or more chest electrodes are added on the back side of the device, and one or more corresponding additional leads are recorded and used in diagnostic algorithms. Also, the effectiveness will not be affected if front electrodes are pressed with palms or any other part of hands instead with the fingers.

In order to prevent turning the device upside down during the recording procedure, so that the upper side is facing toes of the patient, instead of facing his head, which would lead to a useless recording, either upper or front side of the device may be clearly identified and/or formed, (including being marked) to be easily distinguishable by the patient, for example by a LED diode indicating the current phase of recording.

The handheld cardiac device may be configured as a stand-alone device incorporating an ECG recording module including amplifiers and AD convertor, data storage module, communication module operating on GSM, WWAN, or a similar telecommunication standard for communication with the remote processor (e.g., PC computer, pad, smartphone, etc.) and circuitry (e.g., Wi-Fi, Bluetooth, etc.) for communicating the diagnostic information to the user. Alternatively, it can be realized as a modified mobile phone that includes measuring electrodes and the recording module. Furthermore, it can be realized as a device that is attached to the mobile phone as a case or interchangeable back cover. The attached device incorporates measuring electrodes and the recording module and communicates with the mobile phone using a connector or a wireless connection such as Bluetooth or ANT.

If the device is configured as modified mobile phone or as a device attached to a mobile phone, the hand electrodes may be mounted on the display side of a mobile phone. The hand electrodes can be integrated in the edges of the display side of the phone, or as conductive areas incorporated in a transparent layer covering the display of the phone, arranged in the same way as hand electrodes in the preferred embodiment, and marked with a special color when an cardiac signals measuring application is active.

The signal processing and diagnostic software can also be run on the processor (e.g., microprocessor) including a processor integrated in the handheld device, instead of running on a remote processor (e.g., PC computer). In this case, the communication of recorded information to the remote computer may no longer be required, except for data and processing backups. Also, when the diagnostic processing is carried out by a remote processor, a backup version of the software running on the microprocessor may be integrated in the handheld device, and may be used in situations when the user is in a zone without wireless network coverage.

Also described herein are methods and apparatuses for automated detection of AMI (or ischemia, the underlying physiological process). These automated systems may include three cardiac leads that are substantially orthogonal contain the majority of diagnostic information that is present in the conventional 12-lead ECG. Each user may be registered in the diagnostic system by performing the first transmission of his/her non symptomatic cardiac recording with 3 cardiac leads. This first recording may be used as a reference baseline recording for AMI detection in the diagnostic recording (diagnostic recording meaning any further recording of the 3 cardiac leads of the same user). The availability of the reference baseline cardiac recording may allow distinguishing new from old ST segment elevation (STE) or equivalent parameter), and also other cardiac signal changes suggesting an AMI, providing a tool for automated AMI detection that may have diagnostic accuracy comparable to human ECG interpreters.

The optimal placement of the handheld devices described herein is typically on the chest is with center of the device on the left side of the chest approximately above the center of the heart muscle. In this position, the right edge of the device may be about 3 cm away from the midsternal line, the vertical middle line of the sternum, and the lower edge of the device is at about level of the lower end of the sternum. In an ideal case, the user chooses the optimal position on the chest in the first baseline recording and repeats this position in each future diagnostic recording. In such situation, the cardiac recordings are repeatable, and it is easy to detect cardiac signal changes suggesting an AMI.

In some variations, an adhesive may be used. Thus the apparatus may include an adhesive material or an adhesive patch or dock may be used to connect to reproducibly connect to the apparatus and hold it in a predetermined position on the user. For example, the same recording position of the electrodes during the baseline recording and any further test recording can be achieved using a self-adhesive patch with (or connecting to a device with) the chest electrodes. A self-adhesive patch with the chest electrodes may be attached for the first recordings and remains on the same place on the user chest. Similarly, a patch to which the apparatus may dock to place the electrodes in a predetermined location may be used. The user needs to touch the hand electrodes.

In a realistic case, the user may place the device at a position that is different compared to the baseline position, which may compromise diagnostic accuracy. This misplacement is equivalent to a virtual change of the heart electrical axis in the 3D vector space defined by the 3 cardiac leads. In some variations, this angular change may be calculated for each test recording compared to baseline recording. If the angular change is greater than a threshold, such as 15 degrees, the user may be alerted to choose a position that is closer to the baseline position. If the change is lower than the threshold, it may be compensated for by rotating the signal loops of the test recording in the 3D vector space and get the signal that is substantially equivalent to the baseline signal.

Although switching of the left and right finger or turning the device upside down is not very likely (due to asymmetric electrode configuration and configuration of the apparatus, e.g., by clear marking of the upper or front side of the device), it may still be possible. In this case all three signals may become unusable. Both of these user errors may be easily detected, since in both cases the signal of the lead recorded between the left and the right hand may become inverted. In such case, the user may be alerted to repeat the recording using the correct recording position.

The method for automated detection of AMI (or ischemia) may, in some variations, the following steps: placing the device in a recording position on the user chest; acquisition of a first 3 lead cardiac recording and communicating the signals to the processing unit; storage of the first recording in the data base of the processing unit as baseline recording for further comparison with any subsequent diagnostic recording; acquisition of the 3 lead cardiac diagnostic recording and communicating the signal to the processing unit, and processing of the resulting signals. Processing of the stored baseline signals and signals of the diagnostic recordings by the processing unit may include the following steps: pre-processing to eliminate power line interference, baseline wandering and muscle noise, obtain representative beat using fiducial points and median beat procedure, check for switching of the left and right finger, beat alignment to bring baseline and test recordings' representative beats in the same time frame so as the corresponding points are synchronized, compensation for chest electrode mispositioning in recording the test signal by compensating the heart electrical axis deviation in the 3 cardiac leads vector space, calculating difference signal, representing the change between baseline and diagnostic 3 cardiac leads signals, detection of cardiac signal changes suggesting ischemia by comparing the parameters of the test recording to the baseline recording or by comparing parameters on the difference signal to a predefined threshold, communicating information by the processing unit to the device, and finally communicating the diagnostic information by the device to the patient.

The STE is the most common ECG change in case of ischemia, usually measured at the J point or up to 80 msec later. Using STE as a parameter, the ischemic changes may be detected by comparing STE in the test recording to the baseline recording. Also, the ischemic changes may be detected by measuring the vector difference of the ST vector in the vector space defined by the 3 special cardiac leads (STVD), taking the baseline recording as a reference. As mentioned above, although these parameters (e.g., ST, J, STVD, STE), are defined with respect to traditional 12-lead ECG signals, they be herein refer to equivalent measures determined for the three cardiac leads (orthogonal signals) described herein. Thus, these equivalent points, regions or phenomena (e.g., STE, ST, J, STVD, etc.) may be identified by comparison between the cardiac signals described herein and traditional ECG signals, including traditional 12-lead ECG signals.

Other parameters of the cardiac signals may also be used for comparison with the baseline reference signal, such the "Clew", defined as the radius of the sphere which envelopes the vector signal hodograph between J and J+80 msec points.

Cardiac signals for an individual are highly repeatable as far as their shape is concerned. The changes of the signal shape are generally small for a healthy, or an individual in stable condition. For example, the change of the position of the heart with respect to rib cage can change the heart electrical axis by up to 10°. However, there are conditions when the signal shape may change over time, like STE caused by the Benign Early Repolarization (BER). Such signal changes are highly individual and could be significant. To compensate for such changes, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) may be defined as a distance from the 3D contour instead from the baseline ST vector. If more than one parameter is used for ischemia detection, such a reference contour may be constructed as a hyper-surface in a multi-dimensional parameter space defined by such parameters. In this case a hyper-distance from the reference hyper-surface will be defined in the said parameter space.

In some conditions, the signal shape changes may also be intermittent (the condition "comes and goes"), like in Brugada syndrome, WPW syndrome, Bundle Branch Blocks (BBB), etc. To compensate for signal changes in such conditions, two groups of baseline recordings (e.g., at least two recordings) may be used to define the reference, one with normal signals and one with the said intermittent condition present. These two groups will form two 3D contours in the vector space, forming a reference for comparison. These two 3D contours may overlap or not. If there is no overlap, the ST vector difference (STVD) will be defined as a distance from closest point on the two 3D contours. If more than one parameter is used for AMI/ischemia detection, such reference contours would be constructed as two hyper-surfaces in a multidimensional parameter space defined by such parameters. In this case a hyper-distance from the reference hyper-surface will be defined in the said parameter space.

Primary use of the methods described herein may be applied to the detection of the most urgent cardiac diagnosis—the AMI. Additionally, the diagnostic methods (e.g., software) in the remote processor (or integrated processor in the handheld device) can detect other cardiac conditions such as chronic Coronary Arthery Disease (CAD), Left Ventricular Hypertrophy (LVH), Bundle Branch Blocks (BBB), Brugada syndrome, rhythm disorders such as Atrial Fibrillation (AF) etc.

Although the methods described herein do not require the reconstruction of conventional 12 lead ECG recordings, they may be used to reconstruct them. In many of the above mentioned conditions to be detected, treatment may be urgently needed, although to a lesser extent compared to AMI. Also, many of such conditions are transient, and may be detected using here described technology, but may not be present when the user later comes to the physician's office. In such a case, it would be useful to present the ECG signals for the condition that was discovered at the time of recording, so that physician may use it to confirm the diagnosis. Physicians are familiar with the conventional 12 lead ECG recording. Therefore, 3 special cardiac leads recorded when the condition was discovered may be transformed to produce an approximate reconstruction of conventional 12 lead ECG recording. Such reconstruction may be obtained by multiplication of the 3 special cardiac leads with a 12×3 matrix. This matrix may be obtained as a population matrix, that is a matrix with coefficients that are calculated as average, or median, values of individual matrices obtained by simultaneously recording conventional 12 lead ECG and 3 special cardiac leads in a population of individuals, with each individual matrix obtained using least squares method. The coefficients of such matrices are dependent of the shape of the user's body. Therefore, instead of using a single population matrix, multiple matrices may be used, each for a group of users defined by simple parameters of the body shape and structure, like gender, height, weight, chest circumference, etc., that may be easily obtained by the user. Also, matrix coefficients may be obtained as continuous functions of such body parameters.

Figure 1B:
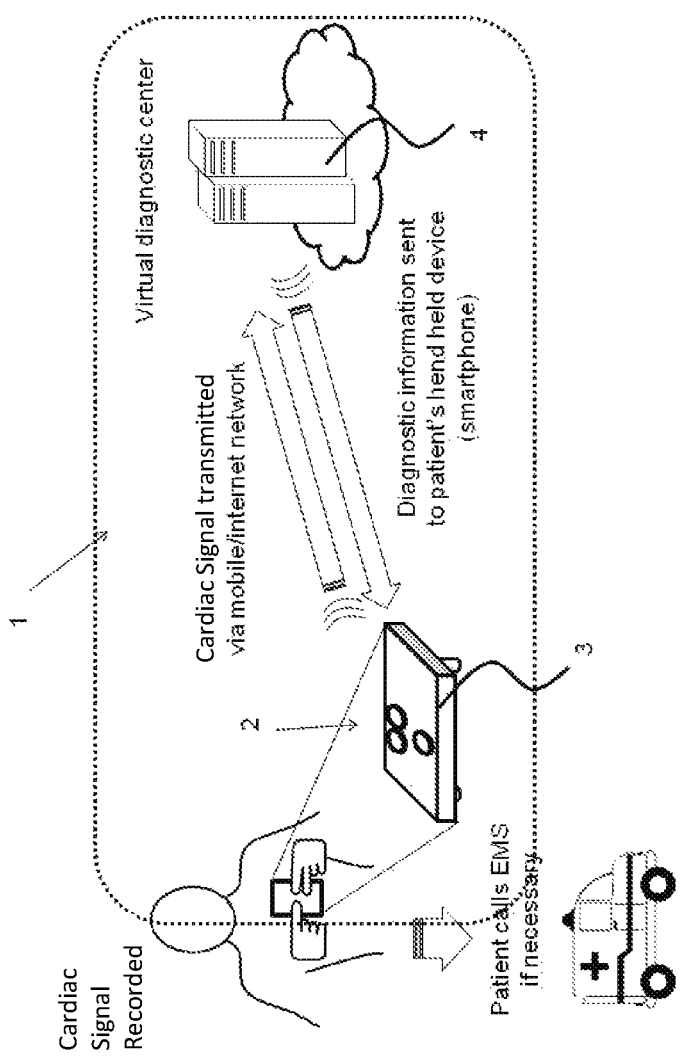
FIG. 1B is another schematic of a remote diagnostic system, wherein the processor is remote from the hand-held device.

FIG. 1A illustrates one variation of a method of operating a system for cardiac signal detection and/or diagnosis. In FIG. 1A, the user 2 may record cardiac signals (e.g., at two or more times), and the apparatus 3 may process the three orthogonal leads to compare the different times (e.g., baseline vs. assay time). The processor of the apparatus 3 may further determine if the resulting differential signal indicates that cardiac problem, and can alert the user. The user (patient) can then get medical assistance as necessary. FIG. 1B shows a view of anther variations of a system and method for detecting cardiac dysfunction, including a system 1 for remote diagnostics of AMI including handheld device 2 incorporating built in electrodes for cardiac signal acquisition, mounted directly on the casing 3 of the hand held device and a PC computer 4 connected via a telecommunication link to the device.

The device further incorporates an cardiac signal recording circuitry including amplifiers and AD convertor for amplifying the signals detected by the electrodes, data storage (e.g., memory) for storing the recording signal, communication circuitry operating on GSM, WWAN, or a similar telecommunication standard for communication with the remote processor 4 and visual and/or audio (e.g., monitor, speaker, etc.) for communicating the diagnostic information to the user.

The device may be communicating with the remote processor 4 via integrated communication circuitry. The remote processor 4 may communicate with the handheld device 2 via integrated communication module. The processor 4 may be equipped with diagnostic software for processing the received cardiac signals, producing diagnostic information and for transmitting the information back to the handheld device for communicating the diagnostic information to the patient via microphone producing characteristic sounds or voice messages or in the form of graphical information via a display integrated in the device. As a consequence, the system may be capable of performing automated detection of a cardiac condition on the basis of a 3-lead system and doesn't require interpretation of the processed diagnostic information by a specialist. Alternatively, instead of a remote processor, the system may include a microprocessor integrated in the casing 3 of the hand held device for processing the recorded cardiac signals and producing diagnostic information.

FIGS. 2A, 2B and 2C show front, back and axonometric views, respectively, of the preferred embodiment of the hand held device. FIG. 2A shows the front view 5 of the device 2 in the recording position as held by the user. The casing 3 of the device may incorporate four recording electrodes A, B, C, D, and one ground electrode G arranged in such arrangement that enables recording of three special ECG lead signals. On the flat back surface 5 of the device in this example are mounted two recording electrodes, A and B, used to make contact with the chest of the patient in the recording position. The two chest electrodes, A and B, are preferably arranged to cover distance greater than at least 5 cm, preferably greater than about 10 cm in caudal direction. The reason for having such spaced arrangement is to achieve the distance greater than approximate diameter of the heart muscle which is needed to approach as much as possible lead orthogonality.

In addition to the two chest electrodes, A and B, the device in this example has two recording electrodes, C and D, mounted on the flat front surface 6 substantially parallel and opposite to the back surface 5. These electrodes, C and D, are used for recording cardiac signals of the hands by pressing with fingers of the left and right hand respectively. The fifth electrode G serves as grounding electrode and is mounted on the front surface 6 for pressing with a left hand finger.

Referring back to FIG. 2A, there is shown a view of the preferred embodiment of the invention in recording position. For operation, the user (e.g., patient) places the device in his left hand so that patient's index and middle finger contact electrodes C and G respectively, positions and presses the device against his chest so that the chest electrodes A and B contact his chest in the manner shown in FIG. 2E for producing tight contact between chest and the device. This may produce enough pressure for holding the device against the chest. Simultaneously, a finger of the right hand (or any other part of the right hand) presses the reference electrode D mounted on the front surface 6 of the casing 3.

Referring back to FIG. 2D there is shown a front view of the device placed against the patient's body in recording position according to the preferred embodiment of the invention. In an optimal recording position the center of the device is placed closely above the center of the heart so that the chest electrodes A and B are approximately on the midclavicular line (the vertical line passing through the midpoint of the clavicle bone), and the lower chest electrode B is at about the level of the lower end of the sternum.

Figure 3:
FIG. 3 shows a simple electrical scheme for obtaining a central point CP by connecting the electrodes of both hands via a simple resistive network with two resistors.

The example in FIG. 3 shows a simple electrical scheme for obtaining a central point CP by connecting the electrodes of both hands via a simple resistive network with two resistors.

Figure 4A:
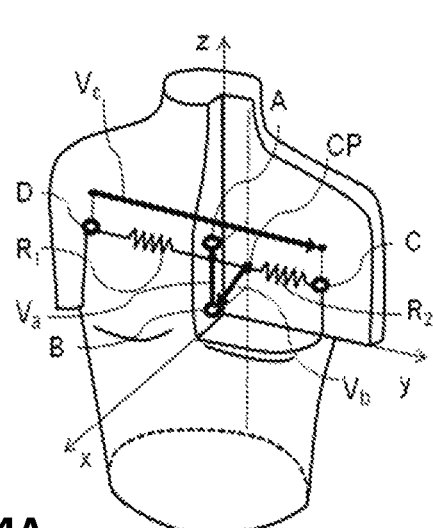
FIG. 4A shows schematic configuration of the three cardiac leads measured on the torso with one lead using central point as the reference pole—the preferred embodiment.

FIG. 4A shows a spatial view of the lead configuration according to one embodiment, illustrating the arrangement of active electrodes A, B, C, D with respect to the body, as well as relative arrangement between the electrodes. FIG. 4B shows a simplified electrical scheme illustrating the same relative arrangement between the electrodes shown in FIG. 4A. For recording a lead in approximately sagittal direction, the voltage of the lower chest electrode B with respect to a central point CP may be obtained using the hand electrodes C, D and two resistors R1, R2. The two resistors R1, R2 can be equal, approximately 5 k$\Omega$ each, or unequal, approximately 5 k$\Omega$ between the left hand electrode and the CP, and 10 k$\Omega$ between the right hand electrode and the CP. This asymmetry may reflect the left-side position of the heart in the torso, thus putting the CP point at the approximate electrical center of the heart. In this way a substantially orthogonal three lead configuration may be obtained.

Figure 4C:
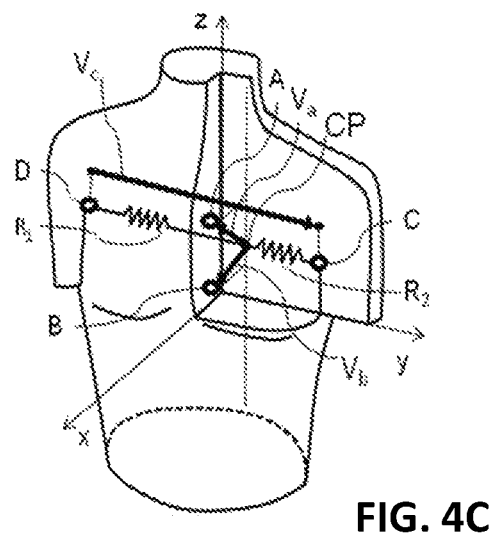
FIG. 4C shows a schematic configuration of the three cardiac leads measured on the torso with two leads using central point as the reference pole.
Figure 4B:
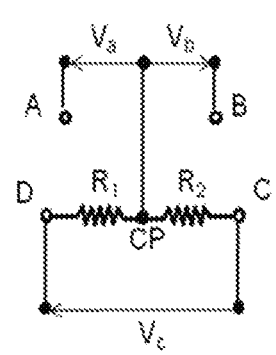
FIG. 4B shows an electrical circuit of the three cardiac leads with one lead using central point as the reference pole.
Figure 4D:
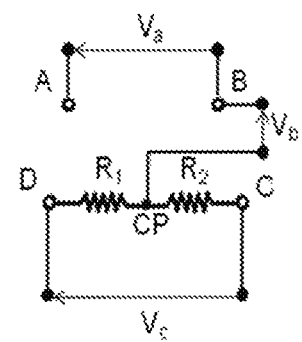
FIG. 4D is an electrical circuit of the three cardiac leads with two leads using central point as the reference pole.

FIG. 4C shows a spatial view of an alternative lead configuration with the central point CP using the same set of chest and hand electrodes A, B, C, D, illustrating arrangement of the electrodes with respect to the body, as well as relative arrangement between the electrodes. FIG. 4D shows simplified electrical scheme illustrating the same relative arrangement between the electrodes A, B, C, and D, shown in the FIG. 4C. This alternative lead configuration using a central point CP and measuring two leads between the CP and each of the chest electrodes is also substantially orthogonal, since the chest electrodes A, B are used to record leads with the reference pole at the CP which is obtained using two hand electrodes C, D and two resistors R1, R2.

Other lead configurations without central point CP and resistors may also be used, like the configuration shown in FIG. 4E, recording the signal of two chest electrodes and right hand electrode with respect to left hand electrode. Other two similar configurations are shown in FIGS. 4F and 4G. Such configurations without resistors are subject to less external interference, such as 50-60 Hz electrical noise, but have less orthogonal lead directions than the previously described ones using a CP. Generally, any other lead configuration using the same four described electrodes may result in non-coplanarity and, as such, captures the diagnostic signal in all three directions, but lacks high orthogonality. There are a total of 20 possible configurations without a CP, including ones shown in FIGS. 4E, 4F and 4G. However, these configurations have different levels of orthogonality, depending on the use of the right hand electrode. The configuration using the right hand electrode as the common reference pole in all 3 leads have the lowest orthogonality, since the right hand electrode is farthest from the heart among the four electrodes, and thus the angles between the vectors corresponding to the three leads are the smallest. The configurations using right hand electrode in two leads, such as the configuration shown in FIG. 4F, have better orthogonality, while best orthogonality is achieved in the configurations using right hand electrode in only one lead, such as the configurations shown in FIGS. 4E and 4G.

FIGS. 5A, 5B and 5C show front view, back view and an axonometric view, respectively, of an alternative embodiment of the hand held device, whereby FIG. 5A shows the front view of the device in the recording position as held by the user. In the alternative embodiment, the electrode D1 for recording cardiac signal of the right arm by pressing with finger of the right hand is mounted on the flank 71 of the casing 31, instead on the front surface 61 as in the embodiment described above. Active recording electrodes A1 and B1 for recording cardiac signal of the patient's chest are mounted on the back surface 51 of the device in the same manner as in the embodiment above. An active recording electrode C1 for recording cardiac signal of the left hand by pressing with finger of the left hand and ground electrode G1 for pressing with another finger of the left hand are mounted on the front surface 61 also in the same manner as above.

The finger switching may be prevented by having an asymmetric electrode configuration, so that the right hand electrode cannot be wrongly pressed by the left hand, and vice versa. However in each of the embodiments (preferred and alternative), the upper (facing head) and lower part (facing toes) of the device may be easily distinguished, since turning the device upside down would lead to wrong recording. This may be done by integrating LED diodes in either upper or front side of the device, indicating the current recording phase, in the front surface of the device casing.

The handheld cardiac device may be realized as a standalone device incorporating an cardiac signals recording circuitry including amplifiers and AD convertor, data storage circuitry (memory), communication circuitry operating on GSM, WWAN, or a similar telecommunication standard for communication with the remote PC computer and an output for communicating the diagnostic information to the user (e.g., screen, speaker, etc.). In so embodiments, the apparatus may be configured to operate with a modified mobile phone that includes measuring electrodes and the cardiac signal recording capability. Furthermore, the apparatus can be realized as a system that is attached to a mobile phone (smartphone) as a case or interchangeable back cover. The attached device may incorporate measuring electrodes and the cardiac signal recording module (including electrodes, balancing circuit, etc.) and communicates with the mobile phone using a connector or a wireless connection such as Bluetooth or ANT.

FIGS. 6A, 6B and 6C show a front view, back view and axonometric view, respectively, of another alternative embodiment of the hand held device. On the back side 52 of the device 32 there are electrodes A2, B2 are mounted for touching the chest of the patient conducting the recording in the same manner as in the preferred embodiment. On the front side 62 of the device there are three electrodes, an active electrode C2, a reference electrode D2 and a ground electrode G2. All three electrodes C2, D2 and G2 have elongated, beam or band like shape and are integrated on the front side 62 of the device, preferably along the two longer, parallel edges of the housing 32 so as to be partially accessible from the sides. In the recording position, the electrodes C2, D2 and G2 are touched by fingers of the left and right hand, in the manner equivalent to the one shown for electrodes C, D and G shown in FIG. 2A, respectively. This electrode arrangement is suitable if the device is realized as a modified mobile phone that includes measuring electrodes and the cardiac signal recording module, or if it is realized as a device that is attached to the mobile phone as a case or interchangeable back cover. In such embodiment, the elongated electrodes may be a part of the frame surrounding the display of the mobile phone or tablet.

Beside, this alternative electrode arrangement, featuring two electrodes on one side and on electrode on the opposite side, fulfills the requirement of asymmetry as well, needed for avoiding finger switching.

In another alternative embodiment, the device is a modified mobile phone that includes recording electrodes and the cardiac signal recording module, with a touch screen. The three hand electrodes for pressing with hands or fingers are realized as transparent conductive areas incorporated in a transparent layer covering the display of the phone, arranged in the same way as hand electrodes in the preferred embodiment. The smart phone application will mark the conductive areas on the screen with a special color when the cardiac signal recording application is active.

In another alternative embodiment, the device contains self-adhesive patch with the chest electrodes. The self-adhesive patch is attached on the user chest enabling the same chest electrode positions for the baseline and all subsequent diagnostic recordings as described above. Alternatively or additionally, the apparatus (e.g., system) may include a patch having a docking region for connecting with any of the electrode-including devices described herein, that may be used to connect (or provide fiduciary reference for) the device to the same location on a user's chest. For example, a docking adhesive patch may include a mating component or region that connects to the device to hold the chest electrodes on the device in a reproducible location on the user's chest. In some variations, the docking adhesive comprises a Band-Aid type material that is worn by the user over an extended period of time (e.g., hours, days, weeks), and may be replaced with another adhesive to maintain the same reference location.

Figure 7:
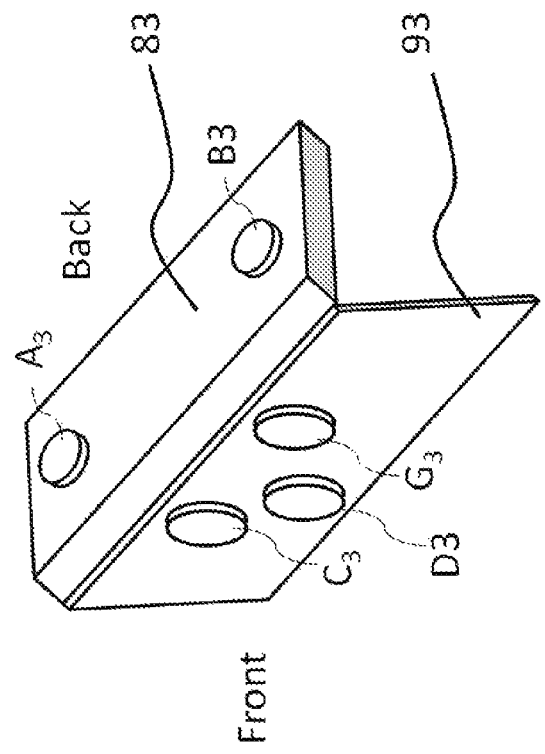
FIG. 7 is an axonometric view of the handheld device realized as a flip case attachable to a mobile phone.

FIG. 7 shows another embodiment of the device realized as an extension 83 to a mobile phone, such as a case or interchangeable back cover, having a form of a so called flip case or wallet for mobile phone, incorporating chest electrodes A3 and B3 on the back side of the device, and the left and right hand finger electrodes C3 and D3 incorporated in the flip-type phone display cover 93 of mobile phone casing.

Figure 8:
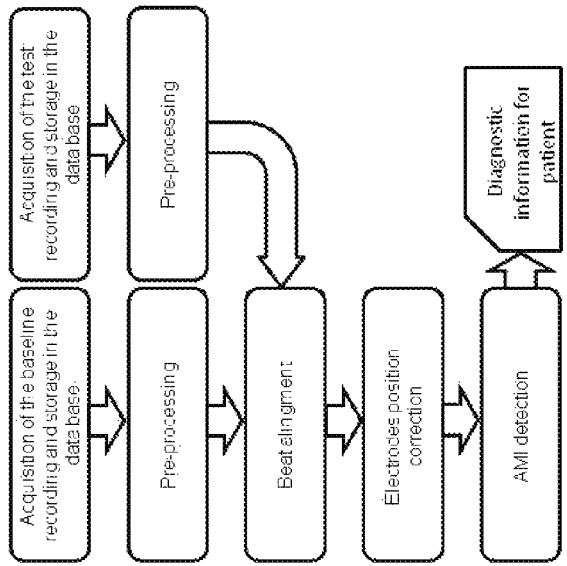
FIG. 8 shows a flow chart of the method for detecting AMI.

FIG. 8 shows a block diagram of the method for automated detection of AMI according to the preferred embodiment of the invention. A method for automated detection of AMI (or ischemia) may include all or some of the steps described below. First, placing the device in a recording position on the user chest.

An optimal position of the handheld device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum. The user presses one active electrode and one ground electrodes with the fingers of the left hand and one active electrode with the finger of the right hand on the front side of the device.

The method may also include acquisition of a first 3 lead cardiac recording and communicating the signals to the processing unit. The user of the automated AMI diagnostic system may perform the recording of the 3-lead cardiac signal by holding the handheld device against the chest for a short period of time (e.g., at least 30 seconds, at least 20 seconds, at least 10 seconds, at least 5 seconds, etc.). The recording is stored in the memory of the device and then transmitted to the remote PC computer via commercial communication network.

The method may also include storage of the first recording in the data base of the processing unit as a baseline. After performing the first transmission of his/her cardiac signal, the cardiac signal recording is stored in a remote processor, and the user may be registered in the diagnostic system. Before this first transmission, the user or his MD/nurse may enter (via a dedicated web site) his medical data such as age, gender, risk factors for cardiovascular disease, etc., and indicate if he/she is currently having chest pain or any other symptom suggesting ischemia. If the answer is negative, this first cardiac recording is kept in the diagnostic system as a baseline recording that will serve as a reference for comparison in any further transmission when symptoms suggesting ischemia may occur.

The method may further include acquisition of the 3 lead cardiac diagnostic recording and communicating the signal to the processing unit. Any subsequent recording after the baseline recording has been accepted and stored in the data base is considered to be diagnostic recoding. The user of the automated AMI diagnostic system performs the diagnostic recording of the 3-lead cardiac signal by holding the handheld device against the chest for at least 10 seconds. The diagnostic recording is stored in the memory of the device and then transmitted to the remote PC computer via commercial communication network.

In general, the methods described herein may include processing of the stored signals of baseline and diagnostic recordings by the processing unit. Processing may include pre-processing. For example the apparatus/method may be configured to let Va,Vb,Vc be the 3 special leads recorded using the handheld device. Before performing any analysis, cardiac signal must be "cleaned" from the disturbing factors like power line interference, baseline wandering and muscle noise. While the former two may be removed using standard adaptive filtering and cubic spline techniques, respectively, the latter is suppressed using time-averaging median beat procedure.

To create a median beat, the entire cardiac signal may be delineated, resulting in set of fiducial points $S=\{P_1, P_2, \ldots, P_n\}$, where $P_i=\{Q_i, R_i, J_i, T_i, T_{i,end}\}$ (or points equivalent to these locations) are fiducial points of i-th beat. Based on S, the signal is then divided into n individual beats of the same length. Finally, individual beats are synchronized using cross-correlation (CC) and for each sample median value across all n beats is calculated. Thus, the entire cardiac signal is represented by the single most-representative median beat. A set of fiducial points $P=\{Q, R, J, T, T_{end}\}$ associated to the median beat are simply calculated as median values of the fiducial point of the individual beats.

Techniques for obtaining representative beat other than median beat may also be used. The delineation of the cardiac signal resulting in fiducial points for each beat may be done using different techniques like wavelet transform, support vector machine, etc.

The same pre-processing procedure is used for both baseline and diagnostic recording.

If the lead recorded between the left and the right hand, or other lead capturing the signal in the lateral direction, is inverted, the user is alerted to repeat the recording using the correct recording position.

The processing may also include beat alignment. For example, the apparatus or method may be configured to let B and D denote to the median beats extracted from the baseline and diagnostic cardiac signals, respectively, and PB and PD are their associated fiducial points. The goal of beat alignment is to bring B and D in the same time frame so as the corresponding points are accurately synchronized. This involves finding of such transformed B, referred to as B*, so that it is optimally synchronized to the D. The applied transformation is piece-wise uniform re-sampling of B, so that corresponding segments in B* and D, defined by PB and PD, respectively, have the same number of samples. Optimal alignment is obtained by searching for such fiducial points PB* that optimize cost function or similarity measure (SM) which quantifies the alignment:

$$P_B^* = \underset{P_B}{\arg opt} SM \tag{1}$$

B* is then obtained by transforming B using the $P_B^*$.

In the present embodiment, we used CC which is commonly used SM for shape-based alignment problems. However, use of solely CC may lead to wrong alignment as shape in B and D may be significantly different. Therefore, we introduce weighting functions $f_{wi}$, which penalizes large deviations from the $P_B$, as the fiducial points $P_B$ are assumed to be accurately known:

$$f_{wi} = e^{-\left(\frac{\Delta P_{Bi}}{c_i}\right)^2} \tag{2}$$

where i=Q, R, J, T, $T_{end}$, $\Delta P_{Bi}$ is deviation from the i-th fiducial point and ci is scaling factor which depends on the fiducial points. Namely, as the R point is the most stable reference in cardiac signal, its deviation is penalized the most. On the other hand, as J and $T_{end}$ points are the least stable, thus, larger deviations are allowed. The overall SM is then calculated as product of CC and sum of weighting functions $f_{wi}$:

$$SM = CC(B(P_B),D)\Sigma_{i=1}^{5} f_{wi}(|P_B - P_{Bi}|) \quad (3)$$

Finally, according to the Eq. (1) the B* is obtained by finding optimum of SM given in Eq. (3).

The processing may also include compensation for chest electrode mispositioning. During regular use of the handheld device, chest electrodes may not be placed on the same spot every time, thus leading to changes in shape of cardiac signal even in absence of any pathology. This change can be modeled as "virtual" heart electrical axis deviation in the Va,Vb,Vc leads vector space if lead positions are assumed to be constant, with the heart electrical axis represented by the R vector—the heart vector at the moment of maximal magnitude in the QRS complex (or equivalent region in the three-lead cardiac signals described herein). However, this is undesired property as the difference signal ΔD will be significant, even though there are no pathologically induced changes. To overcome this problem, we transform D, resulting in D*=TD, so that its heart electrical axis overlaps with the axis of B*. The transform T is calculated using least squares method and Q-J segment (QRS complex) of D and B* as input.

In general, processing may also include calculating difference signal, representing the change between baseline and diagnostic3 cardiac leads signals. The difference signal ΔD* is calculated as:

$$\Delta D^* = D^* - B^* \quad (4)$$

Ultimately, such difference signal ΔD* will reflect solely pathologically induced changes and it will be independent on heart axis deviation.

Since the quality of the device misplacement compensation decreases with increase of the angle heart axis deviation, if the angular change is greater than a threshold, such as 15 deg, the user is prompted to choose a position that is closer to the baseline position.

The processing methods and apparatus described herein may also include detection of ischemic changes. The STE is the most common ECG change in case of ischemia, measured usually at the J point or up to 80 msec later. In the present solution, the ischemic changes are detected by comparing the test recording to the baseline recording. In the preferred embodiment, the parameter or "marker" for ischemia detection is STVM (or equivalent region in the cardiac signals described herein), the vector magnitude of the corrected difference signal ΔD* at 80 msec after the J point (J+80 msec), compared to a predefined threshold, such as 0.1 mV.

In other embodiments, vector magnitude in other time points may be used as marker for ischemia, such as J point, J+60 msec, T max, etc. Other markers may be used that describe the shape of the ST segment (ECG signal segment between J and J+80 msec points, or similar). Such a marker is the "Clew", defined as the radius of the sphere which envelopes the vector signal hodograph between J and J+80 msec points. Also, other composite markers may be used, such as a logistic regression using a linear combination of STVM and Clew markers.

To compensate for signal shape change over time, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) will be defined as a distance from the 3D contour instead from the baseline ST vector. If more than one parameter is used for ischemia detection, such a reference contour would be constructed as a hyper-surface in a multidimensional parameter space defined by such parameters. In this case a hyper-distance from the reference hyper-surface will be defined in the said parameter space.

In users having cardiac condition with intermittent signal shape changes, compensation for such changes may be done by forming two groups of baseline recordings (at least two recordings) to define the reference, one with normal signals and one with the said condition. These two groups will form two 3D contours in the vector space, forming a reference for comparison, and the ST vector difference (STVD) will be defined as a distance from closest point on the two 3D contours. If more than one parameter is used for ischemia detection, such reference contours would be constructed as two hyper-surfaces in a multidimensional parameter space defined by such parameters. In this case a hyper-distance from the reference hyper-surface will be defined in the said parameter space.

Any of these methods and apparatuses may be configured for communicating information by the processing unit to the device. The created diagnostic information may be transmitted from the remote processor (e.g., a PC computer, server, etc.) to the device memory via commercial communication network. The method and apparatuses may also be configured for communicating the diagnostic information by the device to the patient. The received diagnostic information may be presented to the user in a form of characteristic sound, voice, graphics or text.

Additionally, an approximate conventional 12 lead ECG signal may be sent to the user's physician for evaluation. This signal may be produced as an approximate reconstruction of conventional 12 leads by transforming the 3 special cardiac leads signals recorded by the user. This reconstruction may be obtained by multiplication of the 3 special cardiac leads with a 12×3 matrix. In one embodiment, this matrix may be obtained computationally by using a general solution of potentials distribution on the surface of the human body, similar to those previously described for defining a conventional vector cardiogram. In another embodiment, this matrix may be obtained as a population matrix, that is a matrix with coefficients that are calculated as an average, or median, values of individual matrices obtained by simultaneously recording conventional 12 lead ECG and 3 special cardiac leads in a population of individuals, with each individual matrix obtained using least squares method. In yet another embodiment, multiple matrices may be used in corresponding user groups defined by simple parameters of the body shape and structure, like gender, height, weight, chest circumference, etc., that may be easily obtained by the user. Also, matrix coefficients may be obtained as continuous functions of such body parameters.

Device Positioning

The optimal placement of the handheld devices described herein is typically on the chest is with center of the device on the left side of the chest approximately above the center of the heart muscle. In this position, the right edge of the device may be about 3 cm away from the midsternal line, the vertical middle line of the sternum, and the lower edge of the device is at about level of the lower end of the sternum. In an ideal case, the user chooses the optimal position on the chest in the first baseline recording and repeats this position in each future diagnostic recording. In such situation, the cardiac recordings are repeatable, and it is easy to detect cardiac signal changes suggesting an AMI.

In an alternative embodiment, the cardiac data may also be acquired using the other existing hand-held device, disclosed in patent document [U.S. Pat. Nos. 7,647,093, 7,647,093 Bojovic et al], mentioned above. The device is capable of recording and transmitting three special cardiac leads to a remote diagnostic center for reconstruction of 12 standard ECG leads that serve as an cardiac signals input to risk scoring method. In this alternative embodiment, the cardiac signals of two chest electrodes and left-hand electrode are obtained with respect to right hand electrode, i.e. where the right-hand electrode is common reference point for the remaining recording leads (left hand and two chest electrodes), as described in patent document [U.S. Pat. No. 7,647,093 Bojovic et al].

Methods of Risk Assessment

A risk assessment model for evaluating patient's probability of having a serious condition such as Acute Myocardial Infarction (AMI) or cardiac ischemia is based on three types of input data: a) patient's risk factors, b) cardiac signals recording and c) current symptoms data.

The assessment method may comprise the following steps: 1) entering the risk factors data by patient himself and storing data in the system memory; 2) self-recording three lead ECG by the patient using hand-held device; 3) entering current symptoms data by the patient himself; 4) sending cardiac signals and current symptoms data to the remote processor/server; 5) processing data on the processor/server; 6) sending diagnostic message to the hand-held device; 7) communicating the diagnostic message to the patient using graphical or voice interface of the hand-held device. Step 1 is performed during the first use of the device/system by the patient. Steps 2-7 are performed when the patient is having symptoms or wants to do a cardiac check-up. The diagnostic message may refer to calling the emergency service, waiting for another measurement or ignoring the symptoms. In other words, the message has a form of instructions for the patient about what action actions to take.

In some embodiments, the automatic diagnostic system is based on cardiac risk evaluation using three risk components: cardiac signals risk (CSR), pre-existing risk (PER—patient's risk factors stored in the memory) and chest pain risk (CPR—current symptoms risk). Each risk is described with three risk levels: H—High, I—Intermediate, L—Low. The cardiac risk evaluation value is used to choose the diagnostic message communicated to the patient.

The final diagnostic message to the patient is given after up to 3 repeated diagnostic sessions 5-10 min apart. Each diagnostic session consists of cardiac signals recording and chest pain questionnaire (CPQ).

Cardiac Signals Risk (CSR):

Evaluation of cardiac signals risk may include three cardiac leads that are substantially orthogonal and contain the majority of diagnostic information that is present in the conventional 12-lead ECG. Each user may be registered in the diagnostic system by performing the first transmission of his/her non-symptomatic cardiac recording with 3 cardiac leads. This first recording may be used as a reference baseline recording for AMI detection in the diagnostic recording (diagnostic recording meaning any further recording of the 3 cardiac leads of the same user). The availability of the reference baseline cardiac recording may allow distinguishing new from old STE (ST segment elevation), and also other cardiac signal changes suggesting an AMI.

The STE is the most common ECG change in case of ischemia, measured usually at the J point or up to 80 msec later. In the present solution, the ischemic changes are detected by comparing the diagnostic recording to the baseline recording. In the preferred embodiment, the parameter or "marker" for ischemia detection is STVM, the vector magnitude of the difference signal $\Delta D^*$ at 80 msec after the J point (J+80 msec), representing the change between baseline and diagnostic 3 cardiac leads vector. The difference signal $\Delta D^*$ is calculated as (as discussed above, equation (4)):

$$\Delta D^* = D^* - B^*$$

Where $D^*$ is diagnostic 3 cardiac leads vector, and $B^*$ is baseline 3 cardiac leads vector.

In other embodiments, vector magnitude in other time points may be used as marker for ischemia, such as J point, J+60 msec, T max, etc. Other markers may be used that describe the shape of the ST segment (ECG signal segment between J and J+80 msec points, or similar). Such a marker is the "Clew", defined as the radius of the sphere which envelopes the vector signal between J and J+80 msec points. Also, other composite markers may be used, such as a logistic regression using a linear combination of STVM and Clew markers.

In some embodiments, automatic detection of cardiac signals signs of ischemia may be based solely on the diagnostic recording, without using the baseline recording. This approach may be used in case of a patient that is not the owner of the automatic device, and thus his baseline recording is not stored in the device's memory. In this case, the value of $B^*$ (baseline 3 cardiac leads vector) may be simply set to zero.

In some embodiments, automatic detection of cardiac signals signs of ischemia may be based on the conventional approach [Kligfield, Recommendations for the Standardization and Interpretation of the Electrocardiogram, Circulation. 2007; 115:1306-1324] where the main signs of ischemia are ST segment shift and T wave inversion. These parameters or "markers" of ischemia are defined on conventional 12 lead ECG. The conventional 12 lead ECG may be synthesized from three orthogonal leads by using matrix transform, using an individual matrix as described in patent document [U.S. Pat. No. 7,647,093 Bojovic et al] or population baseline matrix.

The thresholds to classify CSR (H—High, I—Intermediate, L—Low) are defined as following: H—when CSR marker value is above the threshold (TH2). This threshold may correspond to the criterion for STEMI based on 12 lead ECG, such as 0.2 mV; I—when CSR marker value is between TH1 and TH2, where TH1 may be the optimal threshold for separation AMI vs. non-AMI signals, such as 0.1 mV; L—when CSR marker value is below TH1.

The threshold TH1 and TH2 may be determined from the previous experience and medical literature, or may be optimized using the cardiac signals recordings from a clinical data set.

Pre-Existing Risk (PER): (H—High, I—Intermediate, L—Low)

In the preferred embodiment, the pre-existing risk (PER) evaluation algorithm is based on the 2013 ACC/AHA Guideline on the Assessment of Cardiovascular Risk [Goff D C Jr, Lloyd-Jones D M, Bennett G, et al.: 2013 ACC/AHA guideline on the assessment of cardiovascular risk: a report of the American College of Cardiology/American Heart Association Task Force on Practice Guidelines. Circulation. 2014; 129 (suppl 2):549-573]. The variables that statistically merited inclusion in the risk assessment equations were age, total cholesterol, high-density lipoprotein cholesterol, systolic BP (including treated or untreated status), diabetes mellitus (diabetes), and current smoking status. Ten-year risks of atherosclerotic cardiovascular disease (ASCVD) events estimates are used for cutoffs between low (L for <5%), intermediate (I for 5-10%), and high (H for >10%) risk levels. For calculation the pre-existing risk (PER) variable, a "Pooled Cohort Equation" of exponential type is used:

$$PER = 1 - BaselineSurvival^{e^{(IndividualSum-MeanSum)}} \quad (5)$$

Where using the coefficients values are established on a cohort of more than 20,000 patients and published in [Goff D C Jr, Lloyd-Jones D M, Bennett G, et al.: 2013 ACC/AHA guideline on the assessment of cardiovascular risk: a report of the American College of Cardiology/American Heart Association Task Force on Practice Guidelines. Circulation. 2014; 129 (suppl 2):S49-S73], for example BaselineSurvival=0.9144 and MeanSum=61.18 for male patients.

The variable IndividualSum is calculated as a linear combination of individual risk factors:

$$IndividualSum = C1*\ln(Age) + C3*\ln(TotalCholesterol) + C4*\ln(Age)*\ln(TotalCholesterol) + C5*\ln(HDL) + C6*\ln(Age)*\ln(HDL) + C7*TreatedSystolicBP*\ln(SystolicBP) + \ln(HDL) + C9*(1-TreatedSystolicBP)*\ln(SystolicBP) + C11*Smoker - C12*\ln(Age)*Smoker + C13*Diabetes$$

Where coefficients C1-C13 and corresponding risk factor values are used corresponding predetermined values (such as, but not limited to, those shown in [Goff D C Jr, Lloyd-Jones D M, Bennett G, et al.: 2013 ACC/AHA guideline on the assessment of cardiovascular risk: a report of the American College of Cardiology/American Heart Association Task Force on Practice Guidelines. Circulation. 2014; 129 (suppl 2):S49-S73], herein incorporated by reference in its entirety.

Alternative scores may be used for pre-existing risk (PER) evaluation, such as Framingham CHD risk score [Marma A K, Lloyd-Jones D M. Systematic examination of the updated Framingham Heart Study general cardiovascular risk profile. Circulation. 2009; 120:384-90] and the European SCORE (System for Cardiac Operative Risk Evaluation) [Perk J, De Backer G, Gohlke H, et al. European Guidelines on cardiovascular disease prevention in clinical practice (version 2012). The Fifth Joint Task Force of the European Society of Cardiology and Other Societies on Cardiovascular Disease Prevention in Clinical Practice, Eur Heart J. 2012; 33:1635-701], each of which is herein incorporated by reference in its entirety.

Chest Pain Risk (CPR): (H—High, I—Intermediate, L—Low)

Chest pain risk (CPR—current symptoms risk) parameters are entered manually by the patients at the time the cardiac symptoms occur by means of a keyboard or touch screen. The chest pain risk parameters are chosen based on literature data and inventor's own clinical experience.

In the preferred embodiment, a list of nine parameters-questions is used as shown in FIG. 9. Each answer to a question is assigned with a specific number of points, between −1 and 3, also shown in FIG. 9. The value of CPR variable is calculated as sum of points for all nine parameters-questions.

The CPR risk level is estimated with cutoffs between low (L for <2 points), intermediate (I for 2-5 points), and high (H for >5 points) risk levels.

In other embodiments, alternative questions/answers, number of points or cutoff values may be used.

Post-Test AMI Risk (PTR): (H—High, I—Intermediate, L—Low)

Post-test AMI risk (PTR) evaluation is based on using three risk components: cardiac signals risk (CSR), pre-existing risk (PER) and chest pain risk (CPR) and can have three levels (H—High, I—Intermediate, L—Low). There are 27 possible combinations of CSR, PER and CPR values. The PTR value for each of these combinations is established based on literature data and inventor's own clinical experience. The values of all 27 possible combinations and corresponding PTR values are given at the FIG. 10.

Diagnostic Reports (Messages)

The diagnostic report is given to the patient after completing a diagnostic assessment that may have one, two or three diagnostic sessions (the cardiac signals recording and filling the chest pain questionnaire) performed by the patient in predefined time intervals, such as three sessions with 5-10 minutes time intervals.

The diagnostic report given to the patient may consist of different diagnostic messages suggesting the action that a patient should take. For example, the diagnostic message may suggest that the patient seeks medical help immediately, or Reassure regarding the benign nature of the symptoms. In the preferred embodiment, there are six possible messages: (1) The diagnostic system shows that you are having a heart attack. Call emergency service immediately. (2) The diagnostic system shows that probability of heart attack is high. You need to call emergency service and go the Emergency Room. (2A) You might be experiencing angina. Try to relax in quiet position, take a Nitro and repeat recording in 5 min. If the pain gets worse or lasts longer than your typical angina call emergency service. (3) Your chest pain episode might be a sign of a heart problem. You should notify your doctor and discuss whether further testing is necessary. If pain comes back call emergency service. (3A) The diagnostic system shows that you had an episode of angina. According to diagnostic system assessment the pain has resolved and ECG is back to normal. If this episode felt like your usual angina no urgent action is required. If the pattern of angina (severity, frequency, duration of pain) changes you need to notify your physician urgently. (4) Based on the diagnostic system assessment your chest pain is most likely not related to your heart. You should mention it to your doctor on your next appointment. Use your judgment to seek medical care if pain continues.

The messages 2A and 3A are used only for patients having angina pectoris as reported while filling their pre-existing risk (PER) questionnaire.

Diagnostic assessment by default has three sessions. The diagnostic assessment may be terminated with less than three sessions if conditions for termination the diagnostic assessment are satisfied.

In the preferred embodiment, the diagnostic message is chosen based on PTR (Post-test risk), CSR (cardiac signals risk), existence of chest pain, pre-existence of angina pectoris and the following set of rules:

Decision Rules

1. Score CSR=H in the 1st, 2nd or 3rd session terminates the diagnostic assessment and produces Message 1.

2. Scores PTR=H and CSR<H in the 1st, 2nd or 3rd session terminates the diagnostic assessment and produces Message 2.

3. Scores PTR<H sends request for additional session when the current number of completed sessions is less than 3.

4. After 3rd session, if PTR=I in any of the sessions and CP=1 (chest pain persists) in 3rd session, then Message 2 is produced.

5. After 3rd session, if PTR=I in any of the sessions and CP=0 (chest pain stopped) in 3rd session, then Message 3 is produced (only for non-angina patients).

6. After 3rd session, if PTR=L in all of three sessions and CP=0 (chest pain stopped) or CP=1 (chest pain persists) in 3rd session produces Message 4.

7. Patients with angina and scores PTR=H and CSR<H in the 1st or 2nd session produces Message 2A.

8. Patients with angina and score CSR=I or CSR=H in the 3rd session and CP=0 (chest pain stopped) produces Message 3.

9. Patients with angina and scores PTR=I or PTR=H in any of the 1st and 2nd sessions and CSR=L and CP=0 in the 3rd session produces Message 3A.

Figure 11:
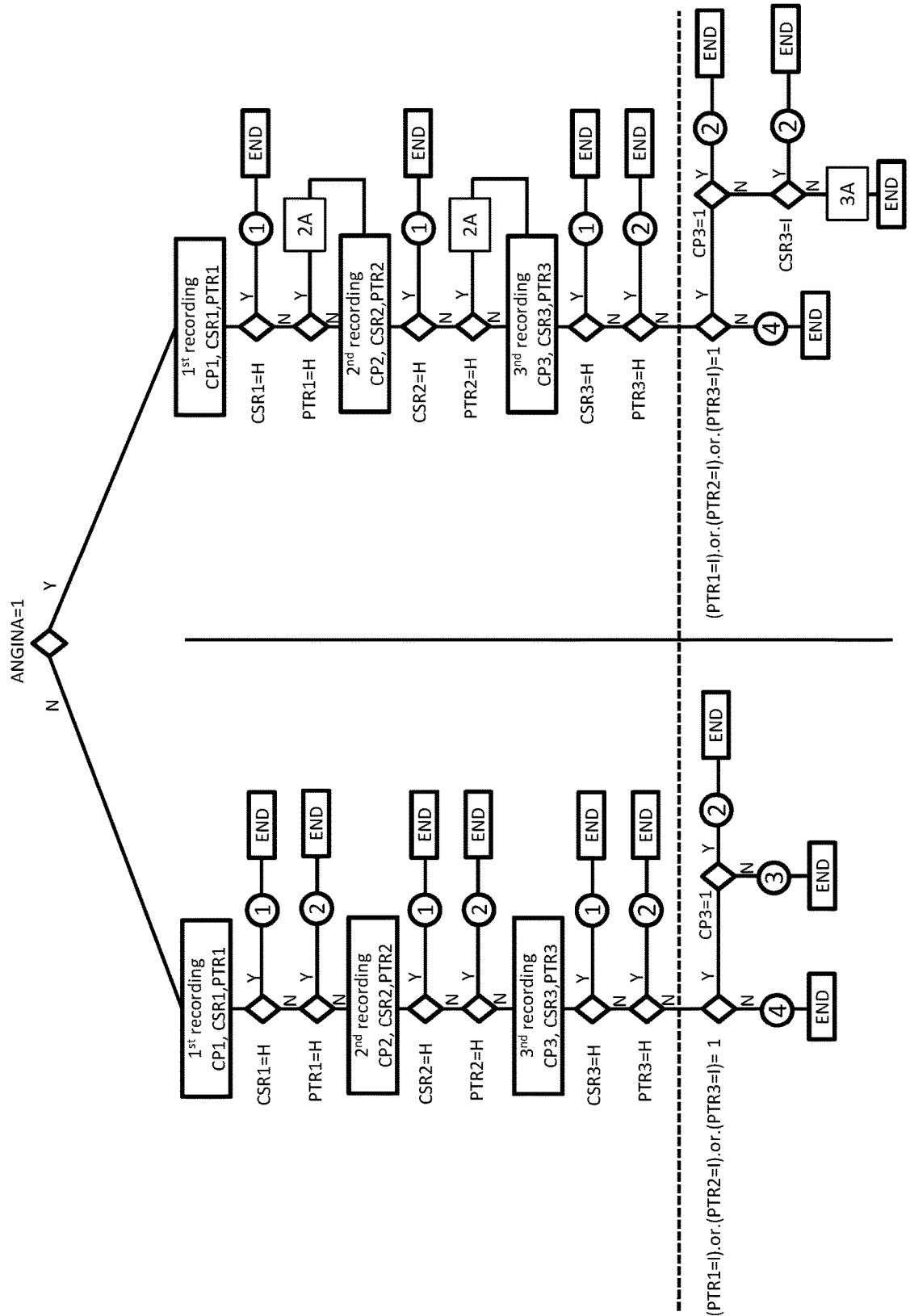
FIG. 11 is a process flow illustrating one method of indicating, to a patient, risk and treatment advice, as described herein.

FIG. 11 depicts the flowchart of the algorithm based on the above described rules 1-9. The flowchart has two branches for patients without and with angina. Each branch has three recording sessions with possible exits defined by rules 1-2 and assessment based on the completed three recording sessions according to the rules 3-9. After the any exit algorithm produces messages 1-4 (in the circles on the FIG. 11) related to AMI assessment or messages 2A and 3A (in the rectangles on the FIG. 11) related to the angina episodes.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of automatically assessing a patient's risk of an acute cardiac event, the method comprising:
    receiving, from the patient, risk assessment information comprising risk factors, wherein the risk assessment information is received by a processor;
    storing a pre-existing risk score based on the risk assessment information;
    receiving, from the patient, a sample electrocardiogram (ECG), wherein the patient self-records the sample ECG using a handheld apparatus, and receiving, from the patient, a current symptoms indication, wherein the current symptoms indication includes a plurality of self-reported patient symptoms;
    determining, in the processor, an ECG risk score from the sample ECG and a baseline ECG, and a chest pain risk score indicating a level of cardiac risk based on the current symptoms indication, and using the ECG risk score, the pre-existing risk score, and the chest pain risk score to determine a post-test risk score, wherein the ECG risk score is classified into at least one intermediate category based on a comparison of a voltage difference between the sample ECG and the baseline ECG to a first threshold voltage and a second threshold voltage, wherein the first threshold voltage is less than the second threshold voltage; and
    presenting, to the patient, a diagnostic report and patient action instruction based on the post-test risk score.

2. The method of claim 1, further comprising: receiving in the processor, from the patient more than 24 hours before receiving the sample ECG, the baseline ECG, wherein the patient uses the handheld apparatus to acquire the baseline ECG.

3. The method of claim 1, further wherein the risk factors include: age, total cholesterol, HDL, systolic blood pressure, diabetes mellitus status, and current smoking status.

4. The method of claim 3, wherein the pre-existing risk score based on the risk assessment information comprises a calculated weighted sum of the risk factors.

5. The method of claim 1, wherein receiving, from the patient, the sample ECG comprises the patient using the handheld apparatus, wherein the handheld apparatus has at least four electrodes, to acquire three substantially orthogonal leads.

6. The method of claim 1, wherein receiving, from the patient, the current symptoms indication comprises selecting the current symptoms indication from a predetermined list of symptom selectable on the handheld apparatus.

7. The method of claim 6, wherein the selecting comprises selecting from a user interface on the handheld apparatus, the current symptoms indication.

8. The method of claim 1, wherein determining the chest pain risk score comprises indicating a risk that is high (H), intermediate (I) or low (L).

9. The method of claim 1, wherein determining the post-test risk score comprises applying a look-up table indexed by the ECG risk score, chest pain risk score and pre-existing risk score.

10. The method of claim 1, wherein the step of receiving the sample ECG and the current symptoms indication is repeated prior to determining the ECG risk score.

11. The method of claim 1, wherein the first threshold is associated with a separation of acute myocardial infarction (AMI) and non-AMI ECG differences and the second threshold is associated with a separation of STEMI and non-STEMI ECG differences.

12. The method of claim 1, wherein the ECG risk score is associated with a first classification when the sample ECG is greater than the second voltage, is associated with a second classification when the sample ECG is between the first threshold voltage and the second threshold voltage and is associated with a third classification when the sample ECG is less than the first threshold voltage.

13. A method of automatically assessing a patient's risk of an acute cardiac risk, the method comprising:
    receiving, from the patient at a first time, a baseline electrocardiogram (ECG), wherein the patient uses a wireless handheld apparatus having at least four electrodes to acquire three substantially orthogonal leads, wherein the baseline ECG is received by a processor;

storing the baseline ECG in a first memory accessible to the processor;

receiving, from the patient at a second time, risk assessment information, wherein the risk assessment information is received by the processor;

storing a pre-existing risk score based on the risk assessment information in a second memory accessible by the processor;

receiving, from the patient at a third time that is more than a day from the first time, a sample ECG, wherein the patient self-records the sample ECG using the wireless handheld apparatus and a current symptoms indication, wherein the current symptoms indication is selected from a predetermined list of symptom selectable on the wireless handheld apparatus;

determining, in the processor, an ECG risk score from the sample ECG and the baseline ECG, and a chest pain risk score indicating a level of cardiac risk based on the current symptoms indication, and using the ECG risk score, the pre-existing risk score, and the chest pain risk score to determine a post-test risk score, wherein the ECG risk score is classified into at least one intermediate category based on a comparison of a voltage difference between the sample ECG and the baseline ECG to a first threshold voltage and a second threshold voltage different from the first threshold voltage; and presenting, to the patient, a diagnostic report and patient action instruction based on the post-test risk score.

14. A method of automatically assessing a patient's risk of an acute cardiac risk, the method comprising:

receiving, from the patient at a first time, a baseline electrocardiogram (ECG), wherein the patient uses a wireless handheld apparatus having at least four electrodes to acquire three substantially orthogonal leads, wherein the baseline ECG is received by a processor;

storing the baseline ECG in a first memory accessible to the processor;

receiving, from the patient at a second time, risk assessment information comprising risk factors including: age, total cholesterol, HDL, systolic blood pressure, diabetes mellitus status, and current smoking status, wherein the risk assessment information is received by the processor;

storing a pre-existing risk score based on the risk assessment information in a second memory accessible by the processor;

repeating, when the patient is experiencing cardiac distress at a third time that is more than a day from the first time, the steps of:

receiving, from the patient, a sample ECG, wherein the patient self-records the sample ECG using the wireless handheld apparatus and a current symptoms indication, wherein the current symptoms indication is selected from a predetermined list of symptoms selectable on the wireless handheld apparatus;

determining, in the processor, an ECG risk score from the sample ECG and the baseline ECG, and a chest pain risk score indicating a level of cardiac risk based on the current symptoms indication, and using the ECG risk score, the pre-existing risk score, and the chest pain risk score to determine a post-test risk score, wherein the ECG risk score is classified into at least one intermediate category based on a comparison of a voltage difference between the sample ECG and the baseline ECG to a first threshold voltage and a second threshold voltage different from the first threshold voltage; and presenting, to the patient, a diagnostic report and patient action instruction based on the post-test risk score.

15. An apparatus comprising non-transitory computer-readable storage medium storing a set of instructions capable of being executed by a processor, a processor configured to execute said instructions in order to:

receive, from a patient data entry subprocessor operated by the patient, risk assessment information comprising risk factors, wherein the risk assessment information is received by a processor;

store a pre-existing risk score based on the risk assessment information;

receive, from a cardiac-signal acquisition subprocessor, a sample of patient's cardiac signal, wherein the patient self-records the sample cardiac signal using a wireless handheld apparatus, receive, from said patient data entry subprocessor operated by the patient, a current symptoms indication, wherein the current symptoms indication include a plurality of self-reported patient symptoms;

generate, a cardiac signals risk score from said sample cardiac signal and from a baseline cardiac signal, wherein the cardiac signal risk score classified into at least one intermediate category based on a comparison of a voltage difference between said sample cardiac signal and the baseline cardiac signal to a first threshold voltage and a second threshold voltage, and a chest pain risk score based on the current symptoms indication, wherein the chest pain risk score indicates a level of cardiac risk, generate a post-test risk score output based on the cardiac signals risk score, the pre-existing risk score, and the chest pain risk score; and control an output subprocessor, based on said post-test risk output, said subprocessor configured to report a diagnostic to the patient.

16. The non-transitory computer-readable storage medium of claim 15, wherein the set of instructions cause the processor to receiving in the processor, from the patient more than 24 hours before receiving the sample cardiac signal, the baseline cardiac signal, wherein the patient uses the wireless handheld apparatus to acquire the baseline cardiac signal.

17. The non-transitory computer-readable storage medium of claim 15, wherein the risk factors include: age, total cholesterol, HDL, systolic blood pressure, diabetes mellitus status, and current smoking status.

18. The non-transitory computer-readable storage medium of claim 17, wherein the pre-existing risk score based on the risk assessment information comprises a calculated weighted sum of the risk factors.

19. The non-transitory computer-readable storage medium of claim 15, wherein receiving, from the patient, the sample cardiac signal comprises the patient using the wireless handheld apparatus, wherein the wireless handheld apparatus has at least four electrodes, to acquire three substantially orthogonal leads.

20. The non-transitory computer-readable storage medium of claim 15, wherein receiving, from the patient, the current symptoms indication comprises selecting the current symptoms indication from a predetermined list of symptom selectable on the wireless handheld apparatus.

21. The non-transitory computer-readable storage medium of claim 15, wherein the receiving comprises receiving from a user interface on the wireless handheld apparatus, the current symptoms indication.

22. The non-transitory computer-readable storage medium of claim 15, wherein determining the cardiac signal risk score comprises indicating a risk that is high (H), intermediate (I) or low (L).

23. The non-transitory computer-readable storage medium of claim 15, wherein determining the chest pain risk score comprises indicating a risk that is high (H), intermediate (I) or low (L).

24. The non-transitory computer-readable storage medium of claim 15, wherein determining the post-test risk score comprises applying a look-up table indexed by the cardiac signal risk score, chest pain risk score and pre-existing risk score.

25. The non-transitory computer-readable storage medium of claim 15, wherein the step of receiving the sample cardiac signal and the current symptoms indication is repeated prior to determining the cardiac signal risk score.

\* \* \* \* \*